(12) United States Patent
To

(10) Patent No.: US 9,119,659 B2
(45) Date of Patent: *Sep. 1, 2015

(54) SAFE CUTTING HEADS AND SYSTEMS FOR FAST REMOVAL OF A TARGET TISSUE

(75) Inventor: John To, Newark, CA (US)

(73) Assignee: OUROBOROS MEDICAL, INC., Fremont, CA (US)

(*) Notice: Subject to any disclaimer, the term of this patent is extended or adjusted under 35 U.S.C. 154(b) by 303 days.

This patent is subject to a terminal disclaimer.

(21) Appl. No.: 13/592,307

(22) Filed: Aug. 22, 2012

(65) Prior Publication Data

US 2013/0144292 A1    Jun. 6, 2013

Related U.S. Application Data

(60) Provisional application No. 61/566,629, filed on Dec. 3, 2011, provisional application No. 61/596,865, filed on Feb. 9, 2012.

(51) Int. Cl.
*A61B 17/32*    (2006.01)
*A61B 17/3205*    (2006.01)
(Continued)

(52) U.S. Cl.
CPC ....... *A61B 17/3205* (2013.01); *A61B 17/32002* (2013.01); *A61B 17/320016* (2013.01);
(Continued)

(58) Field of Classification Search
CPC ............... A61B 17/16; A61B 17/1659; A61B 2017/00261; A61B 17/1671; A61B 17/32075; A61B 17/32053; A61B 17/320708; A61B 17/3205; A61B 17/320016; A61B 2017/320024

USPC ............. 606/79–80, 83–86 R, 159, 167–185, 606/205–211

See application file for complete search history.

(56) References Cited

U.S. PATENT DOCUMENTS

| 177,490 A | 5/1876 | Fones et al. |
| 207,932 A | 9/1878 | Alvord |

(Continued)

FOREIGN PATENT DOCUMENTS

| CA | 2 141 019 | 7/1995 |
| DE | 41 33 073 | 4/1992 |

(Continued)

OTHER PUBLICATIONS

International Search Report for PCT/US2009/051735, Sep. 15, 2009, Spine View, Inc.

(Continued)

*Primary Examiner* — Zade Coley
(74) *Attorney, Agent, or Firm* — Brian S. Boyer; Syndicated Law, PC

(57) ABSTRACT

A safe and efficient cutting heads for removing a target tissue from a subject during a surgical procedure are provided, the cutting heads composing a part of systems that address several problems, including clogging of state-of-the-art systems during removal of such tissue, for example. The target tissue can include any tissue that is accessible through a small surgical opening, for example, a joint tissue such as a meniscus or an intervertebral tissue, such as a nucleus pulposus. The devices can be referred to as orthopedic tissue removal devices having cutting heads associated with vacuum systems, making the systems useful in several procedures, including X-LIF (lateral approach to an intervertebral fusions) procedures, T-LIF (transforaminal approach to intervertebral fusions) procedures, P-LIF (posterior approach to intervertebral fusions), and a percutaneous, transforaminal approach (Kambin triangle access).

24 Claims, 9 Drawing Sheets

(51) Int. Cl.
*A61F 2/44* (2006.01)
*A61B 17/00* (2006.01)
*A61B 19/00* (2006.01)

(52) U.S. Cl.
CPC ......... *A61F2/44* (2013.01); *A61B 2017/00261* (2013.01); *A61B 2017/00738* (2013.01); *A61B 2017/320064* (2013.01); *A61B 2019/481* (2013.01); *A61B 2217/002* (2013.01); *A61F 2002/444* (2013.01)

(56) References Cited

U.S. PATENT DOCUMENTS

| | | | |
|---|---|---|---|
| 3,404,677 A * | 10/1968 | Springer | 600/564 |
| 3,774,613 A | 11/1973 | Woods, Jr. et al. | |
| 3,955,579 A | 5/1976 | Bridgman | |
| 4,061,146 A | 12/1977 | Baehr et al. | |
| 4,309,777 A | 1/1982 | Patil | |
| 4,466,429 A | 8/1984 | Loscher et al. | |
| 4,545,374 A | 10/1985 | Jacobson | |
| 4,573,448 A | 3/1986 | Kambin | |
| 4,603,694 A | 8/1986 | Wheeler | |
| 4,646,738 A | 3/1987 | Trott | |
| 4,711,238 A | 12/1987 | Cunningham | |
| 4,733,665 A | 3/1988 | Palmaz | |
| 4,759,766 A | 7/1988 | Buettner-Janz et al. | |
| 4,796,642 A | 1/1989 | Harris | |
| 4,820,305 A | 4/1989 | Harms et al. | |
| 4,848,342 A | 7/1989 | Kaltenbach | |
| 4,997,432 A | 3/1991 | Keller | |
| 5,030,201 A | 7/1991 | Palestrant | |
| 5,074,871 A | 12/1991 | Groshong | |
| 5,078,723 A | 1/1992 | Dance et al. | |
| 5,100,423 A | 3/1992 | Fearnot | |
| 5,108,404 A | 4/1992 | Scholten et al. | |
| 5,192,327 A | 3/1993 | Brantigan | |
| 5,217,474 A | 6/1993 | Zacca et al. | |
| 5,221,261 A | 6/1993 | Termin et al. | |
| 5,248,297 A | 9/1993 | Takase | |
| 5,285,795 A | 2/1994 | Ryan et al. | |
| 5,286,253 A | 2/1994 | Fucci | |
| 5,313,962 A | 5/1994 | Obenchain | |
| 5,354,311 A | 10/1994 | Kambin et al. | |
| 5,383,884 A | 1/1995 | Summers | |
| 5,395,317 A | 3/1995 | Kambin | |
| 5,396,880 A | 3/1995 | Kagan et al. | |
| 5,411,514 A | 5/1995 | Fucci et al. | |
| 5,437,630 A | 8/1995 | Daniel et al. | |
| 5,439,464 A | 8/1995 | Shapiro | |
| 5,456,689 A | 10/1995 | Kresch et al. | |
| 5,496,269 A | 3/1996 | Snoke | |
| 5,529,580 A | 6/1996 | Kusunoki et al. | |
| 5,556,376 A | 9/1996 | Yoon | |
| 5,556,407 A * | 9/1996 | Wurster et al. | 606/174 |
| 5,569,178 A | 10/1996 | Henley | |
| 5,571,106 A | 11/1996 | Coufal et al. | |
| 5,591,187 A | 1/1997 | Dekel | |
| 5,591,190 A | 1/1997 | Yoon | |
| 5,593,416 A * | 1/1997 | Donahue | 606/170 |
| 5,609,635 A | 3/1997 | Michelson | |
| 5,669,926 A | 9/1997 | Aust et al. | |
| 5,693,063 A * | 12/1997 | Van Wyk et al. | 606/167 |
| 5,695,513 A | 12/1997 | Johnson et al. | |
| 5,762,629 A | 6/1998 | Kambin | |
| 5,830,188 A | 11/1998 | Abouleish | |
| 5,871,462 A | 2/1999 | Yoder et al. | |
| 5,882,329 A | 3/1999 | Patterson et al. | |
| 5,885,258 A | 3/1999 | Sachdeva et al. | |
| 5,885,292 A | 3/1999 | Moskovitz et al. | |
| 5,891,153 A | 4/1999 | Peterson | |
| 5,902,263 A | 5/1999 | Patterson et al. | |
| 5,941,869 A | 8/1999 | Patterson et al. | |
| 5,944,686 A | 8/1999 | Patterson et al. | |
| 5,964,716 A | 10/1999 | Gregoire et al. | |
| 5,968,062 A | 10/1999 | Thomas et al. | |
| 5,976,146 A | 11/1999 | Ogawa et al. | |
| 5,980,552 A | 11/1999 | Pinchasik et al. | |
| 6,001,116 A * | 12/1999 | Heisler et al. | 606/180 |
| 6,007,481 A | 12/1999 | Riek et al. | |
| 6,053,907 A | 4/2000 | Zirps | |
| 6,068,642 A | 5/2000 | Johnson et al. | |
| 6,120,437 A | 9/2000 | Yoon et al. | |
| 6,127,597 A | 10/2000 | Beyar et al. | |
| 6,178,346 B1 | 1/2001 | Amundson et al. | |
| 6,187,000 B1 | 2/2001 | Davison et al. | |
| 6,200,322 B1 | 3/2001 | Branch et al. | |
| 6,216,573 B1 | 4/2001 | Moutafis et al. | |
| 6,280,475 B1 | 8/2001 | Bao et al. | |
| 6,319,242 B1 | 11/2001 | Patterson et al. | |
| 6,325,806 B1 | 12/2001 | Fox | |
| 6,352,539 B1 | 3/2002 | Avellanet | |
| 6,368,351 B1 | 4/2002 | Glenn et al. | |
| 6,371,968 B1 | 4/2002 | Kogasaka et al. | |
| 6,375,635 B1 | 4/2002 | Moutafis et al. | |
| 6,379,346 B1 | 4/2002 | McIvor et al. | |
| 6,511,493 B1 | 1/2003 | Moutafis et al. | |
| 6,524,320 B2 | 2/2003 | DiPoto | |
| RE38,018 E | 3/2003 | Anctil et al. | |
| 6,530,926 B1 | 3/2003 | Davison | |
| 6,575,899 B1 | 6/2003 | Foley et al. | |
| 6,575,978 B2 | 6/2003 | Peterson et al. | |
| 6,592,559 B1 | 7/2003 | Pakter et al. | |
| 6,595,998 B2 | 7/2003 | Johnson et al. | |
| 6,648,894 B2 | 11/2003 | Abdelgany et al. | |
| 6,656,195 B2 * | 12/2003 | Peters et al. | 606/159 |
| 6,666,891 B2 | 12/2003 | Boehm, Jr. et al. | |
| 6,669,710 B2 | 12/2003 | Moutafis et al. | |
| 6,746,451 B2 * | 6/2004 | Middleton et al. | 606/79 |
| 6,780,175 B1 | 8/2004 | Sachdeva et al. | |
| 6,821,276 B2 | 11/2004 | Lambrecht et al. | |
| 6,827,716 B2 | 12/2004 | Ryan et al. | |
| 6,837,891 B2 | 1/2005 | Davison et al. | |
| 6,857,943 B2 | 2/2005 | Kapgan | |
| 6,875,219 B2 | 4/2005 | Arramon et al. | |
| 6,893,464 B2 | 5/2005 | Kiester | |
| 6,899,712 B2 | 5/2005 | Moutafis et al. | |
| 6,916,330 B2 | 7/2005 | Simonson | |
| 6,923,792 B2 | 8/2005 | Staid et al. | |
| 6,960,182 B2 | 11/2005 | Moutafis et al. | |
| 7,001,397 B2 | 2/2006 | Davison et al. | |
| 7,033,317 B2 | 4/2006 | Pruitt | |
| 7,033,369 B2 | 4/2006 | Davison et al. | |
| 7,037,321 B2 | 5/2006 | Sachdeva et al. | |
| 7,048,694 B2 | 5/2006 | Mark et al. | |
| 7,108,705 B2 | 9/2006 | Davison et al. | |
| 7,122,017 B2 | 10/2006 | Moutafis et al. | |
| 7,144,393 B2 | 12/2006 | DiPoto et al. | |
| 7,179,225 B2 | 2/2007 | Shluzas et al. | |
| 7,223,278 B2 | 5/2007 | Davison et al. | |
| 7,232,445 B2 * | 6/2007 | Kortenbach et al. | 606/142 |
| 7,241,297 B2 | 7/2007 | Shaolian et al. | |
| 7,337,538 B2 | 3/2008 | Moutafis et al. | |
| 7,338,495 B2 | 3/2008 | Adams | |
| 7,347,130 B2 | 3/2008 | Pham et al. | |
| 8,000,918 B2 | 8/2008 | Sugiura | |
| 7,431,711 B2 | 10/2008 | Moutafis et al. | |
| 7,621,950 B1 | 11/2009 | Globerman et al. | |
| 7,686,806 B2 | 3/2010 | Rhyne | |
| 7,717,685 B2 | 5/2010 | Moutafis et al. | |
| 7,717,932 B2 | 5/2010 | McFarlin et al. | |
| 7,736,366 B2 | 6/2010 | Abdelgany et al. | |
| 7,803,170 B2 * | 9/2010 | Mitusina | 606/171 |
| D626,233 S | 10/2010 | Cipoletti et al. | |
| 7,854,740 B2 | 12/2010 | Carney | |
| 7,927,361 B2 * | 4/2011 | Oliver et al. | 606/279 |
| 7,951,107 B2 | 5/2011 | Staid et al. | |
| 7,955,355 B2 | 6/2011 | Chin | |
| 7,993,269 B2 | 8/2011 | Donofrio et al. | |
| 8,016,859 B2 | 9/2011 | Donofrio et al. | |
| 8,070,754 B2 | 12/2011 | Fabian et al. | |
| 8,083,767 B2 | 12/2011 | Modesitt | |
| 8,123,750 B2 * | 2/2012 | Norton et al. | 606/80 |
| 8,123,755 B2 | 2/2012 | Johnson et al. | |
| 8,162,966 B2 | 4/2012 | Connor et al. | |

(56) References Cited

U.S. PATENT DOCUMENTS

| | | | |
|---|---|---|---|
| 8,216,317 B2 | 7/2012 | Thibodeau | |
| 8,221,425 B2 | 7/2012 | Arcenio et al. | |
| 8,236,058 B2 | 8/2012 | Fabian et al. | |
| 8,267,939 B2 | 9/2012 | Cipoletti et al. | |
| 8,409,235 B2* | 4/2013 | Rubin | 606/180 |
| 8,454,644 B2 | 6/2013 | McDonnell | |
| 8,663,227 B2 | 3/2014 | To | |
| 2002/0016624 A1 | 2/2002 | Patterson et al. | |
| 2002/0138091 A1 | 9/2002 | Pflueger | |
| 2003/0040763 A1 | 2/2003 | Moutafis et al. | |
| 2003/0074075 A1 | 4/2003 | Thomas, Jr. et al. | |
| 2003/0114875 A1 | 6/2003 | Sjostrom | |
| 2003/0130673 A1 | 7/2003 | Trerotola | |
| 2003/0191474 A1 | 10/2003 | Cragg et al. | |
| 2003/0195551 A1 | 10/2003 | Davison et al. | |
| 2004/0024463 A1 | 2/2004 | Thomas, Jr. et al. | |
| 2004/0193151 A1 | 9/2004 | To et al. | |
| 2004/0236328 A1 | 11/2004 | Paul et al. | |
| 2005/0033292 A1 | 2/2005 | Teitelbaum et al. | |
| 2005/0043589 A1 | 2/2005 | Pruitt | |
| 2005/0065538 A1* | 3/2005 | Van Wyk | 606/159 |
| 2005/0090829 A1 | 4/2005 | Martz et al. | |
| 2005/0159765 A1 | 7/2005 | Moutafis et al. | |
| 2005/0267443 A1 | 12/2005 | Staid et al. | |
| 2005/0267502 A1 | 12/2005 | Hochman | |
| 2006/0030785 A1 | 2/2006 | Field et al. | |
| 2006/0036273 A1 | 2/2006 | Siegal | |
| 2006/0089527 A1 | 4/2006 | Doll et al. | |
| 2006/0196038 A1* | 9/2006 | Van Wyk | 29/557 |
| 2006/0206118 A1 | 9/2006 | Kim et al. | |
| 2006/0229550 A1 | 10/2006 | Staid et al. | |
| 2006/0258951 A1 | 11/2006 | Bleich et al. | |
| 2006/0264957 A1 | 11/2006 | Cragg et al. | |
| 2006/0276821 A1 | 12/2006 | Davison et al. | |
| 2007/0055259 A1 | 3/2007 | Norton et al. | |
| 2007/0055263 A1* | 3/2007 | Way et al. | 606/82 |
| 2007/0060935 A1 | 3/2007 | Schwardt et al. | |
| 2007/0066977 A1 | 3/2007 | Assell et al. | |
| 2007/0106246 A1 | 5/2007 | Modesitt | |
| 2007/0123892 A1 | 5/2007 | Ries et al. | |
| 2007/0149975 A1* | 6/2007 | Oliver et al. | 606/79 |
| 2007/0149990 A1 | 6/2007 | Palmer et al. | |
| 2007/0156020 A1 | 7/2007 | Foley et al. | |
| 2007/0162044 A1 | 7/2007 | Marino | |
| 2007/0162062 A1 | 7/2007 | Norton et al. | |
| 2007/0173939 A1 | 7/2007 | Kim et al. | |
| 2007/0213735 A1 | 9/2007 | Saadat et al. | |
| 2007/0233079 A1 | 10/2007 | Fallin et al. | |
| 2007/0255172 A1 | 11/2007 | Pflueger | |
| 2008/0033465 A1 | 2/2008 | Schmitz et al. | |
| 2008/0051812 A1 | 2/2008 | Schmitz et al. | |
| 2008/0058588 A1 | 3/2008 | Emanuel | |
| 2008/0058842 A1 | 3/2008 | Emanuel | |
| 2008/0071303 A1* | 3/2008 | Hacker et al. | 606/180 |
| 2008/0077148 A1* | 3/2008 | Ries et al. | 606/80 |
| 2008/0114364 A1* | 5/2008 | Goldin et al. | 606/79 |
| 2008/0119846 A1 | 5/2008 | Rioux | |
| 2008/0154275 A1 | 6/2008 | Assell et al. | |
| 2008/0183175 A1 | 7/2008 | Saal et al. | |
| 2008/0208194 A1* | 8/2008 | Bickenbach | 606/79 |
| 2008/0208230 A1 | 8/2008 | Chin et al. | |
| 2008/0221605 A1 | 9/2008 | Saal et al. | |
| 2008/0228192 A1 | 9/2008 | Beyar et al. | |
| 2008/0243028 A1 | 10/2008 | Howard et al. | |
| 2008/0255569 A1 | 10/2008 | Kohm et al. | |
| 2009/0018507 A1 | 1/2009 | Schmitz et al. | |
| 2009/0062872 A1 | 3/2009 | Chin et al. | |
| 2009/0099605 A1 | 4/2009 | Fallin et al. | |
| 2009/0270862 A1* | 10/2009 | Arcenio | 606/79 |
| 2009/0275951 A1 | 11/2009 | Arcenio et al. | |
| 2009/0306692 A1 | 12/2009 | Barrington et al. | |
| 2009/0312763 A1* | 12/2009 | McCormack et al. | 606/83 |
| 2009/0326412 A1 | 12/2009 | Pakter | |
| 2010/0004651 A1 | 1/2010 | Biyani | |
| 2010/0010524 A1 | 1/2010 | Barrington et al. | |
| 2010/0030216 A1 | 2/2010 | Arcenio | |
| 2010/0063538 A1* | 3/2010 | Spivey et al. | 606/208 |
| 2010/0076476 A1 | 3/2010 | To et al. | |
| 2010/0100098 A1* | 4/2010 | Norton et al. | 606/80 |
| 2010/0121153 A1 | 5/2010 | To | |
| 2010/0217268 A1 | 8/2010 | Bloebaum et al. | |
| 2010/0217269 A1 | 8/2010 | Landes | |
| 2010/0228273 A1 | 9/2010 | Staid et al. | |
| 2010/0256619 A1 | 10/2010 | Teitelbaum et al. | |
| 2011/0040315 A1 | 2/2011 | To et al. | |
| 2011/0054507 A1* | 3/2011 | Batten et al. | 606/170 |
| 2011/0087257 A1 | 4/2011 | To et al. | |
| 2011/0098531 A1 | 4/2011 | To | |
| 2011/0098711 A1 | 4/2011 | Batten et al. | |
| 2011/0190753 A1* | 8/2011 | Forrest | 606/27 |
| 2011/0190803 A1 | 8/2011 | To et al. | |
| 2011/0288553 A1 | 11/2011 | Jansen et al. | |
| 2012/0022564 A1 | 1/2012 | Batten et al. | |
| 2012/0065659 A1 | 3/2012 | To | |
| 2012/0071714 A1 | 3/2012 | Jansen et al. | |
| 2012/0083889 A1 | 4/2012 | Purcell et al. | |
| 2012/0101513 A1* | 4/2012 | Shadeck et al. | 606/170 |
| 2012/0209273 A1 | 8/2012 | Zaretzka et al. | |
| 2012/0209386 A1 | 8/2012 | Triplett et al. | |
| 2013/0144292 A1 | 6/2013 | To | |
| 2013/0144320 A1 | 6/2013 | To | |

FOREIGN PATENT DOCUMENTS

| | | |
|---|---|---|
| EP | 0 312 787 | 4/1989 |
| EP | 0 369 936 | 5/1992 |
| EP | 0 484 725 | 5/1992 |
| EP | 0 664 992 | 8/1992 |
| EP | 0 694 280 | 1/1996 |
| EP | 2110087 | 10/2009 |
| FR | 1370580 | 8/1964 |
| JP | H10/24044 A | 1/1998 |
| JP | 2007/117721 A | 5/2007 |
| JP | 2009/095662 | 5/2009 |
| WO | WO 93/25263 | 10/1993 |
| WO | WO 00/56389 | 9/2000 |
| WO | WO 01/22889 | 4/2001 |
| WO | WO 01/91651 | 12/2001 |
| WO | WO 02/055146 | 7/2002 |
| WO | WO 02/098300 | 12/2002 |
| WO | WO 2004/019760 | 3/2004 |
| WO | WO 2004/037097 | 5/2004 |
| WO | WO 2004/073500 | 9/2004 |
| WO | WO 2004/110260 | 12/2004 |
| WO | WO 2006/072941 | 7/2006 |
| WO | WO 2006/093976 | 9/2006 |
| WO | WO 2007/008710 | 1/2007 |
| WO | WO 2007/031264 | 3/2007 |
| WO | WO 2007/100591 | 9/2007 |
| WO | WO 2007/103161 | 9/2007 |
| WO | WO 2007/124130 | 11/2007 |
| WO | WO 2008/060277 | 5/2008 |
| WO | WO 2008/116563 | 10/2008 |
| WO | PCT/US2012/051952 | 8/2012 |
| WO | PCT/US2014/046762 | 7/2015 |

OTHER PUBLICATIONS

Adulkasem, W, et al., Early Experience of Endoscopy-Assisted Anterior Spinal Surgery, Journel of Orthopaedic Surgery, Dec. 2002,10(2), 152-159.

Baron, E.M. et al., Neuroendoscopy for Spinal Disorders: A Brief Review, 2005 [online] [retrieved on Feb. 5, 2013] URL: http://www.medscape.com/viewarticle/520947.

Cardinal Health, AVA*flex*™ Curved Injection Needle, 2007, [online] [retrieved on Feb. 5, 2013]URL: http://www.cardinal.com/us/en/distributedproducts/ASP/BCK9811.asp?cat=med_surg-orig.

Heavner, J.E. et al., Lumbosacral Epiduroscopy Complicated by Intravasular Injection, Anesthesiology, Aug. 2007, 107(2), 347-350.

Igarashi, T. et al, Lysis of Adhesions and Epidural Injection of Steroid/local Anaesthetic During Epiduroscopy Potential Alleviate Low Back and Leg Pain in Elderly Patients with lumbar Spinal Stenosis, British Journal of Anaesthesia, 2004, 93(2),181-187.

(56) References Cited

OTHER PUBLICATIONS

Le Huec, J.C. et al, Endoscope Surgery of the Spine, A review of 4 years? Practice, Maltrise Orthopaedique, Jan. 1999 [online] [retrieved on Feb. 5, 2013] URL http://www.maltrise-orthop.com/viewPage_us.do?id=435.

Nash, T.P., Epiduroscopy for Lumbar Spinal Stenosis, British Journal of Anaesthesia, Feb. 2005, 94(2), 250, author reply 250-151.

Saringer, W.F. et al., Endoscopic Anterior Cervical Foraminotomy for Unilateral Radiculopathy: Anatomical Morphometric Analysis and Preliminary Clinical Experience, J. Neurosurg, Mar. 2003, (Spine 2), 98,171-180.

Yeung, A.T., The Evolution of Percutaneous Spinal Endoscopy and Discectomy: State of the Art, The Mount Sinai Journal of Medicine, Sep. 2000, 67(4), 327-332.

Caliber, www.globusmedical.com, [online] [retrieved on Jul. 27, 2012], URL: http://www.globusmedical.com/mis/166-caliber.

Staxx XD, www.spinewave.com, [online][retrieved on Jan. 27, 2013] URL: http://www.spinewave.com/products/xd_us.html.

International Search Report for PCT/US2010/031448, Jun. 16, 2010, Spine View, Inc.

International Preliminary Report on Patentability for PCT/US2010/031495, Oct. 18, 2011, Spine View, Inc.

International Search Report for PCT/US2010/029826, Apr. 2, 2010, Spine View, Inc.

International Search Report for PCT/US2010/031620, Apr. 19, 2013.

Coalign, www.coalign.com, [online][retrieved on Jul. 27, 2012], URL: http://www.coalign.com/.

ZeusO, www.amendia.com, [online] [retrieved on Jan. 27, 2013] URL: http://www.amendia.com/zeuso.html.

Spineology, www.spineology.com, [online] [retrieved on Jul. 27, 2012] URL: http://www.spineology.com/fb/intl/products/optimesh1500e.html.

PR Newswire, Benvenue Medical Starts Enrolling Patients in the Post-Market LIFT Study on the Luna Interbody Spacer System for Degenerative Disc Disease, Mar. 20, 2012, [online] [retrieved on Jan. 27, 2013] URL: http://www.prnewswire.com/news-releases/benvenue-medical-starts-enrolling-patients-in-the-post-market-lift-study-on-the-luna-interbody-spacer-system-for-degenerative-disc-disease-143441246.html.

U.S. Appl. No. 14/463,631, filed Dec. 3, 2011, To—Related case.

U.S. Appl. No. 61/566,629, filed Dec. 3, 2011, To—Related case.

U.S. Appl. No. 61/596,865, filed Dec. 3, 2011, To—Related case.

International Search Report and written opinion for PCT/US2012/051952, Jun. 6, 2013, Ouroboros Medical, Inc.

International Preliminary Report on Patentability for PCT/US2012/051952, Jun. 6, 2013, Ouroboros Medical, Inc.

U.S. Appl. No. 14/332,318, filed Jul. 19, 2013, To (related case).

Supplementary European Search Report for EP 12853751, Oct. 2, 2014.

International Search Report and written opinion for PCT/US2014/046762, Jan. 22, 2015.

* cited by examiner

A	B

C	D

E

SAFE CUTTING HEADS AND SYSTEMS FOR FAST REMOVAL OF A TARGET TISSUE

CROSS-REFERENCE TO RELATED APPLICATIONS

This application claims the benefit of U.S. Provisional Application No. 61/566,629, filed Dec. 3, 2011, and U.S. Provisional Application No. 61/596,865, filed Feb. 9, 2012, each application of which is hereby incorporated herein by reference in its entirety.

BACKGROUND

1. Field of the Invention

The teachings provided herein are generally directed to a safe and efficient cutting head for removing a target tissue from a subject during a surgical procedure.

2. Description of the Related Art

Intervertebral disc disease is a major worldwide health problem. In the United States alone almost 700,000 spine procedures are performed each year and the total cost of treatment of back pain exceeds $30 billion. Age related changes in the disc include diminished water content in the nucleus and increased collagen content by the 4.sup.th decade of life. Loss of water binding by the nucleus results in more compressive loading of the annulus. This renders the annulus more susceptible to delamination and damage. Damage to the annulus, in turn, accelerates disc degeneration and degeneration of surrounding tissues such as the facet joints.

The two most common spinal surgical procedures performed are discectomy and spinal fusion. These procedures only address the symptom of lower back pain, nerve compression, instability and deformity. The objective of the spinal disc fusion procedure is to restore, maintain and stabilize disc height, and/or reduce back pain. The procedure is generally performed by removing central disc material such and inner annulus, nucleus pulposus and the cartilage on the endplates before replacing with bone graft and a scaffold to effect fusion of the vertebral bodies within the treated disc for height stabilization. This removal process is called a discectomy and is both tedious and frequently inadequate which can result in compromised fusion, as well as traumatic and time consuming due to the large incision and dissections required to expose the disc for discectomy.

In a typical discectomy procedure, a nucleotomy is first performed in which the nucleus is loosened by using a curette or a manual shaver to shear the nucleus loose and then removed using a rigid grasper called a rongeur. The surgeon has to insert the rongeur through an opening in the disc called an anulotomy, grasp nucleus and remove out of the disc and the surgical access, clean the jaws and reinsert for more grasping of disc repeatedly. This process can pose safety issues for tissues in between tool passage such as nerves. Furthermore, disc debris left behind can hinder efficient subsequent tissue removal and insertion of the discectomy tools into the disc. The second step is decortication in which cartilage attached to the bone (cartilaginous endplate) is removed by the use of rigid scrapers such as a curette or a rasp to help promote a strong intervertebral fusion. Peeled cartilage are removed by scooping with a curette and withdrawn out of the body by the use of a rongeur. Tissue debris left behind can also compromise efficiency and effectiveness of the decortication resulting in a weaker fusion. Moreover, corners inside the discs are often hard to reach by current state-of-the art tools, often leaving additional areas of inadequate disc removal.

In addition, state-of-the-art systems using a combination of suction and cutting suffer clogging problems due to excised tissue becoming lodged in the system. One of skill will appreciate that problems with clogging during a surgical procedure can be problematic, and a solution to such clogging problems is highly desired.

Although several advanced tools have been developed, none have addressed all of these issues adequately. One of skill in the art would certainly appreciate a discectomy system that is (i) less tedious and time consuming to use, (ii) less prone to clogging by excised tissue; (iii) safer to the subject undergoing the surgery, and (iv) more effective in promoting a strong intervertebral fusion.

SUMMARY

The teachings provided herein are generally directed to a safe and efficient cutting head for removing a target tissue from a subject during a surgical procedure. The target tissue can include any tissue that is accessible through a small surgical opening, for example, a joint tissue such as a meniscus, in some embodiments, or an intervertebral tissue, such as a nucleus pulposus, in other embodiments.

The cutting head can be tubular with a cutting surface forming at least a first plane on a distal perimeter of cutting head, the cutting head in operable communication with a suction device to excise a target tissue in a manner that facilitates an ease of removal of the tissue with the suction. The cutting surface can be flat, sinusoidal, or serrated, for example, and the first plane of the cutting surface may be at an angle, $\theta_{FP}$, that deviates up to 75° from a position that is orthogonal to the central axis of the cutting head. In some embodiments, the cutting surface can have a second plane may be at an angle, $\theta_{SP}$, that deviates up to 75° from a position that is orthogonal to the central axis of the cutting head. In some embodiments, the cutting head has a cutting blade and a blade guard for guarding a perimeter tissue from the cutting blade.

As such, the teachings include a tubular cutting head for removing a target tissue of a subject. In these embodiments, the cutting head can have an outer perimeter that circumscribes a lumen through the cutting head, the lumen having a central axis. The cutting head can also have a forward cutting blade on a distal edge of the outer perimeter, the forward cutting blade configured for (i) cutting a target tissue in a forward stroke of the cutting head and (ii) directing the cut tissue into the lumen. And, the cutting head can also have a blade guard positioned distal to the forward cutting blade and configured to guard a perimeter tissue from the forward cutting blade upon the forward stroke the blade guard having a width that is smaller than the width of a transverse cross-section of the lumen to facilitate entry of the target tissue into the lumen on the forward stroke.

In some embodiments, the cutting head can have a backward cutting blade for cutting the target tissue in a backward stroke of the cutting head, a transverse cutting blade for cutting the target tissue in a transverse stroke of the cutting head, or a combination thereof. In some embodiments, a transverse cutting blade can be positioned on the blade guard for cutting the target tissue in a transverse stroke of the cutting head.

In some embodiments, the backward cutting blade can be positioned on the distal edge of the outer perimeter for cutting the target tissue in the backward stroke of the cutting head. In some embodiments, the backward cutting blade can be positioned on the blade guard for cutting the target tissue in the backward stroke of the cutting head, the blade guard having a double-edged blade tip point back into the lumen at an angle, $\theta_2$, of greater than 90° to trap and/or cut tissue in the lumen in the backwards stroke of the cutting head.

Since the cutting head can be designed to remove tissue through use of a suction, the teachings are also directed to systems of a cutting head that operably connect the cutting head with a suction assembly. As such, the teachings include a such a surgical, tissue removal system that includes a tubular cutting head for removing a target tissue of a subject. The system can include a cutting head having an outer perimeter that circumscribes a flow of suction through the cutting head; a lumen circumscribed by the outer perimeter, the lumen guiding the flow of suction and having a central axis; a forward cutting blade on a distal edge of the outer perimeter, the forward cutting blade configured for (i) cutting the target tissue in a forward stroke of the cutting head and (ii) directing the cut tissue into the lumen; and, a blade guard positioned distal to the forward cutting blade and configured to guard a perimeter tissue from the forward cutting blade upon the forward stroke the blade guard. In some embodiments, the blade guard can have a width that is smaller than the width of a transverse cross-section of lumen to facilitate entry of the target tissue into the lumen on the forward stroke.

The cutting head can be configured for an operable communication between the lumen and a source of a suction, such that the systems include a suction assembly in operable communication with the cutting head for creating the flow of suction for removing the target tissue through the lumen and out of the subject, the suction assembly comprising a rigid suction tube with a central axis. In some embodiments, the operable communication includes the use of one or more suction ports positioned just proximal to the most proximal point of the distal edge of the out perimeter of the cutting head. In some embodiments, the one or more ports can be located from about 3 mm to about 20 mm proximal to the most proximal point of the distal edge.

In some embodiments, the suction assembly comprises an at least substantially rigid suction tube having a proximal end and a distal end, the distal end in the operable communication with the cutting head, and the distal end configured for communicating with a source of suction for the suction assembly. In some embodiments, the at least substantially rigid suction tube can be formed as a single unit with the cutting head.

In some embodiments, the central axis of the lumen is at an angle, $\theta_1$, ranging from about 5° to about 90° from the central axis of the rigid suction tube, and the forward cutting blade is located about 3 mm to about 25 mm from the vertex of the angle, $\theta_1$.

The system of claim 10, the central axis of the lumen has a point of exit at the forward cutting blade, and the point of exit is located at a transverse distance of about 3 mm to about 25 mm that is orthogonal to the central axis of the rigid suction tube.

In some embodiments, the central axis of the lumen can be at an angle, $\theta_1$, ranging from about 5° to about 90° from a central axis of the flow of suction at the distal end of the suction assembly, and the forward cutting blade can be located about 3 mm to about 25 mm from the vertex of the angle, $\theta_1$. In some embodiments, the operable communication between the cutting head and the suction assembly can be articulating, and the angle can be adjustable. In some embodiments, the operable communication between the cutting head and the suction assembly can be rigid, and the angle can be fixed.

In some embodiments, the central axis of the lumen is at an angle, $\theta_1$, ranging from 1° to 180° from a central axis of the flow of suction at the distal end of the suction assembly, and the forward cutting blade is located 3 mm to 25 mm from the vertex of the angle, $\theta_1$. In these embodiments, additional angle, $\theta_3$, is located 5 mm to 25 mm proximal to $\theta_1$, and angles $\theta_1$ and $\theta_3$ are independently selected to range from about 0° to about 180°, with the limitation that (i) the net angle, $\theta_4$, between the central axis of the lumen of the cutting head and the central axis of a rigid suction tube located proximal to $\theta_3$ ranges from 0° to 90°; and, (ii) the distance between the central axis of the lumen of the cutting head and the central axis of the rigid suction tube ranges from 2 mm to 30 mm.

It should be appreciated that the cutting heads and systems taught herein have a variety of applications known to one of skill. In some embodiments, the target tissue can be a nucleus pulposus, and the perimeter tissue can be an annulus fibrosis, for example.

As such, the teachings are also directed to a surgical, tissue removal system for a discectomy, and the systems can comprise a tubular cutting head for removing a nucleus pulposus from a subject. In these embodiments, the systems can include a cutting head having an outer perimeter that circumscribes a flow of suction through the cutting head; a lumen circumscribed by the outer perimeter, the lumen guiding the flow of suction; a forward cutting blade on a distal edge of the outer perimeter, the forward cutting blade configured for (i) cutting the nucleus pulposus in a forward stroke of the cutting head and (ii) directing the cut nucleus pulposus into the lumen; a backward cutting blade for cutting the nucleus pulposus in a backward stroke of the cutting head; a transverse cutting blade for cutting the nucleus pulposus in a transverse stroke of the cutting head; and, a blade guard positioned distal to the forward cutting blade and configured to guard an annulus fibrosis tissue from the forward cutting blade upon the forward stroke. And, the blade guard can have a width, for example, that is smaller than the width of a transverse cross-section of the lumen to facilitate entry of the target tissue into the lumen on the forward stroke.

The teachings also include a method of removing a target tissue from a subject. In these embodiments, the method can comprise creating an opening in a subject for access to a target tissue; inserting a cutting head taught herein through the opening to access the target tissue in the subject; and, forcing the cutting head in a forward direction on a surface comprising the target tissue to remove the target tissue. The forward direction can include a force vector that moves (i) at least substantially on a plane containing the central axis of the lumen of the cutting head, (ii) at least substantially on the surface comprising the target tissue, and (iii) toward the perimeter tissue that is protected by the blade guard. And, the method can include capturing the target tissue in the lumen of the cutting head, as well as removing the target tissue through the lumen and out of the subject.

In some embodiments, the method comprises forcing a cutting head taught herein in a backward direction on a surface comprising the target tissue to remove the target tissue. The backward direction can include a force vector that moves (i) at least substantially on a plane containing the central axis of the lumen of the cutting head, (ii) at least substantially on the surface comprising the target tissue, and (iii) away from the perimeter tissue that is protected by the blade guard.

In some embodiments, the method comprises forcing a cutting head taught herein in a transverse direction on a surface comprising the target tissue to remove the target tissue. The transverse direction can include a force vector that moves (i) at an angle ranging from about 15° to about 150° from a plane containing the central axis of the lumen of the cutting head, (ii) at least substantially on the surface comprising the target tissue, and (iii) in contact with the perimeter tissue that is protected by the blade guard.

The teachings are also directed to an obturator, guard cannula to protect a subject during entry and exit of an elongated surgical cutting device having a non-linearity. In these embodiments, the guard cannula can comprise an entry hub having an inner perimeter, an outer perimeter, and an irrigation port that communicates between the inner perimeter with the outer perimeter; and, a linear, elongated split-tube having a proximal end, a distal end, and a lumen. In these embodiments, the proximal end of the split-tube can (i) circumscribe at least a portion of the inner perimeter of the hub and (ii) be in operable communication with the irrigation port. In these embodiments, the communication can be operable to receive an irrigation fluid from the irrigation port, the transport of the irrigation fluid to a target tissue including, for example, a movement of the irrigation fluid from the irrigation port to the distal end of the split-tube on a luminal surface of the split-tube.

The distal end of the split-tube can also have any configuration desired by one of skill. For example, the distal end can at least substantially pointed and/or sharp. In some embodiments, the distal end can be at least substantially blunt to avoid damage to an entry tissue upon contact of the distal end with the entry tissue. The split-tube can also have a length ranging from about 10 cm to about 60 cm and a width ranging from about 5 mm to about 16 mm. Moreover, the split in the split-tube can compose a gap having a width ranging from about 4 mm to about 14 mm, the split accommodating a non-linearity in the surgical device.

As described above, the systems taught herein can be used in a variety of procedures for removal of a target tissue from a subject including, for example, removal of a meniscus or a discectomy. In some embodiments, the surgical cutting device used with the guard cannula can be a discectomy device. And, in some embodiments, the entry tissue includes the subject's epithelial tissue, muscle tissue, nerve tissue, connective tissue, a blood vessel, bone, cartilage, or a combination thereof, leading to the nucleus pulposus. As such, the target tissue can include the nucleus pulposus in some embodiments.

The teachings are also directed to a surgical tissue removal kit having a surgical tissue removal system and a guard cannula, using any combination of system and cannula embodiments taught herein. In some embodiments, the kits can be a discectomy kit. As such, in some embodiments, the entry tissue includes the subject's epithelial tissue, muscle tissue, nerve tissue, connective tissue, a blood vessel, bone, cartilage, or a combination thereof, leading to the nucleus pulposus. As such, the target tissue can include the nucleus pulposus in some embodiments.

The teachings are also directed to a method of using the kits to remove a target tissue. In some embodiments, the method comprises creating an opening in a subject for access to a target tissue; inserting the cutting head of the kit through the entry hub and the elongated split-tube of the guard cannula of the kit; inserting the cutting head of the kit through the opening to access the target tissue in the subject while protecting the entry tissue with the blunt, distal end of the split-tube. Otherwise, methods of using the tissue removal systems are the same or similar to those taught herein. One of skill will appreciate having such kits for discectomies, for example, in which the target tissue can be a nucleus pulposus, and the perimeter tissue can be an annulus fibrosis. One of skill will also appreciate having a kit with a guard cannula that helps protect the subject's epithelial tissue, muscle tissue, nerve tissue, connective tissue, a blood vessel, bone, cartilage, or a combination thereof, leading to the nucleus pulposus in such procedures.

One of skill will appreciate that the embodiments taught herein are provided for purposes of outlining general concepts, and that several additional embodiments are included in, and can be derived from, the teachings provided herein.

DETAILED DESCRIPTION OF THE INVENTION

The teachings provided herein are generally directed to a safe and efficient cutting head for removing a target tissue from a subject during a surgical procedure. The target tissue can include any tissue that is accessible through a small surgical opening, for example, a joint tissue such as a meniscus or an intervertebral tissue, such as a nucleus pulposus. In some embodiments, the devices taught herein can be referred to as an orthopedic tissue removal device. In some embodiments, the devices taught herein are useful in X-LIF (lateral approach to an intervertebral fusions) procedures, T-LIF (transforaminal approach to intervertebral fusions) procedures, P-LIF (posterior approach to intervertebral fusions), or a percutaneous, transforaminal approach (Kambin triangle access).

The term "subject" and "patient" can be used interchangeably in some embodiments and refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like.

The cutting head can be tubular with a cutting surface forming at least a first plane on a distal perimeter of cutting head, the cutting head in operable communication with a suction device to excise a target tissue in a manner that facilitates an ease of removal of the tissue with the suction.

The cutting surface can be flat, sinusoidal, or serrated, for example, and the first plane of the cutting surface may be at an angle, $\theta_{FP}$, that deviates up to 75° from a position that is orthogonal to the central axis of the cutting head. In some embodiments, the cutting surface can have a second plane may be at an angle, $\theta_{SP}$, that deviates up to 75° from a position that is orthogonal to the central axis of the cutting head. In some embodiments, the cutting head has a cutting blade and a blade guard for guarding a perimeter tissue from the cutting blade. In some embodiments, $\theta_{FP}$ and $\theta_{SP}$ can be independently selected to range from 0° to about 75°, from about 5° to about 75°, from about 10° to about 70°, from about 15° to about 65°, from about 10° to about 60°, from about 5° to about 55°, from about 15° to about 50°, from about 20° to about 45°, from about 15° to about 40°, from about 25° to about 35°, or any angle or range of angles therein in increments of 1°.

Figure 1:
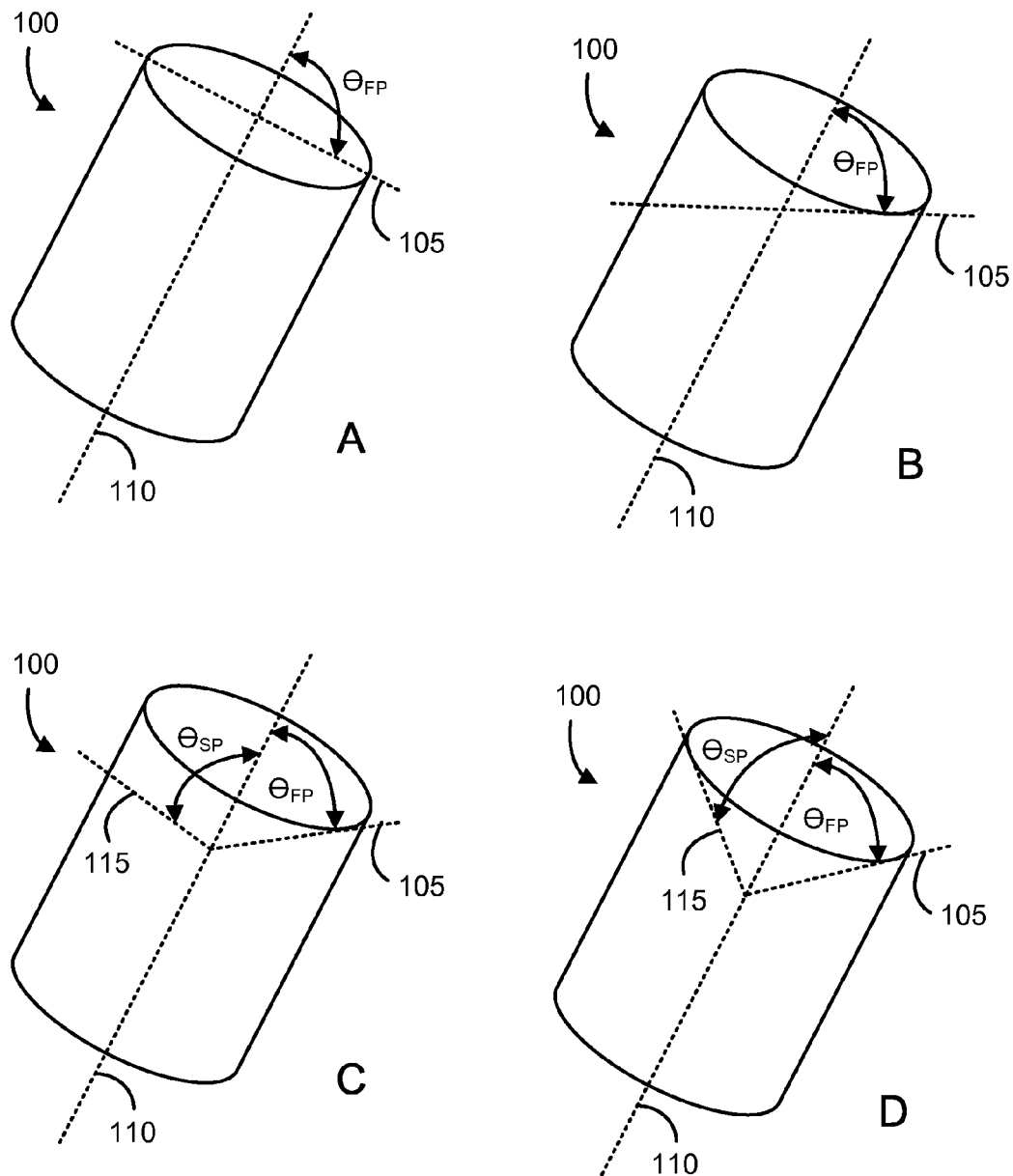
FIGS. 1A-1D illustrates a variety of tubular cutting head configurations that can be fabricated from stock tube, according to some embodiments.

FIGS. 1A-1D illustrates a variety of tubular cutting head configurations that can be fabricated from stock tube, according to some embodiments. FIG. 1A shows a cutting head stock tube 100 having a first plane 105 at an angle, $\theta_{FP}$, that is orthogonal to the central axis 110 of the lumen of the stock tube 100. FIG. 1B shows a cutting head stock tube 100 having a first plane 105 at an acute angle, $\theta_{FP}$, to the central axis 110 of the lumen of the stock tube 100, the acute angle ranging from 1° to about 75°. FIG. 1C shows a cutting head stock tube 100 having a first plane 105 at an acute angle, $\theta_{FP}$, to the central axis 110 of the lumen of the stock tube 100, the acute angle, $\theta_{FP}$, ranging from 1° to about 75°; and, having a second plane 105 at an angle, $\theta_{SP}$, that is orthogonal to the central axis 110 of the lumen of the stock tube 100. FIG. 1D shows a cutting head stock tube 100 having a first plane 105 at an acute angle, $\theta_{FP}$, to the central axis 110 of the lumen of the stock tube 100, the acute angle ranging from 1° to about 75°; and, having a second plane 105 at an angle, $\theta_{SP}$, to the central axis 110 of the lumen of the stock tube 100, the acute angle, $\theta_{SP}$, ranging from 1° to about 75°.

The cutting head can be fabricated from any material known to one of skill to be suitable in a surgical environment for the uses taught herein. For example, a hard material with hardness greater than Rockwell C 30 or greater than Rockwell C 45 can be suitable in some embodiments. In some embodiments, the cutting head can be comprised of a component selected from the group consisting of tempered steel, stainless steel, high carbon steel, titanium or titanium alloy, ceramic, diamond and obsidian. In some embodiments, the stainless steel can comprise 304 stainless steel, 316 stainless steel, 17-4 PH stainless steel, 400 series stainless steel, or any other stainless steels known to one of skill to be suitable for the cutting functions taught herein. In some embodiments, the cutting head can be made of cobalt chromium, tungsten carbide, or a ceramic.

The tube forming the cutting head can have a wall thickness, for example, from 0.003" to 0.020" or more specifically 0.005" to 0.012". The cross-sectional area of the cutting head can range from 0.120 inches$^2$ to 1.5 inches$^2$ or, in some embodiments, from 0.180 in$^2$ to 0.400 in$^2$. The width in any direction can range from 0.080" to 0.400" or more and, in some embodiments, 0.160" to 0.250". In some embodiments, the cutting head can have a maximum transverse cross section dimension ranging from about 3.0 mm to about 20.0 mm, from about 4.0 mm to about 15.0 mm, from about 4.0 mm to about 12.0 mm, from about 5.0 mm to about 10.0 mm, about 5.0 mm to about 8.0 mm, or any range therein in increments of 0.1 mm. In some embodiments, the cutting heads have diameters of about 4.8 mm, about 5.0 mm, about 5.2 mm, about 5.4 mm, about 5.8 mm, about 6.0 mm, about 6.2 mm, about 6.4 mm, about 6.6 mm, about 6.8 mm, about 7.0 mm, about 7.2 mm, about 7.4 mm, about 7.6 mm, about 7.8 mm, about 8.0 mm, about 8.2 mm, and any 0.1 mm increment therein.

The distal perimeter of a cutting head can be on the first plane or the second plane, or a combination thereof, and the cutting surfaces can be any cutting surface known to one of skill, such as a razor surface, a serrated surface, or a sinusoidal surface, in some embodiments. There are a variety of possible blade configurations known to one of skill in the art of cutting blade design, and any such configuration may be used. For example, the cutting surface can have teeth and gullets between the teeth. The spacing between the teeth can be equal or variable, and the depth of the gullets can be equal or variable, and any combination of teeth and gullets can be used. In some embodiments, the direction of the protrusion of the teeth can be offset from the direction of the remainder of the walls of the cutting head. In some embodiments, the teeth are in the same direction as the remainder of the walls of the cutting head, such that the teeth are merely an extension of the walls of the cutting head, with no shift in direction toward the lumen of the cutting head or away from the lumen of the cutting head. In some embodiments, there is a pattern of directional shift of the teeth away from, or toward, the lumen of the cutting head. For example, the pattern can be a sequence of toward, away, toward, away, no shift, and the sequence is repeated around the distal edge of the outer perimeter of the cutting head. In some embodiments, all teeth can point toward the lumen, and in some embodiments, all teeth can point away from the lumen. In some embodiments, the teeth alternate toward the lumen and away from the lumen tooth-by-tooth. And, in some embodiments, the teeth are gradually toward and away from the lumen at gradually increases and decreasing angles, tooth-by-tooth, to create an appearance of waves as the teeth circle the distal edge of the outer perimeter. The sequence can also be entirely random.

Figure 2:
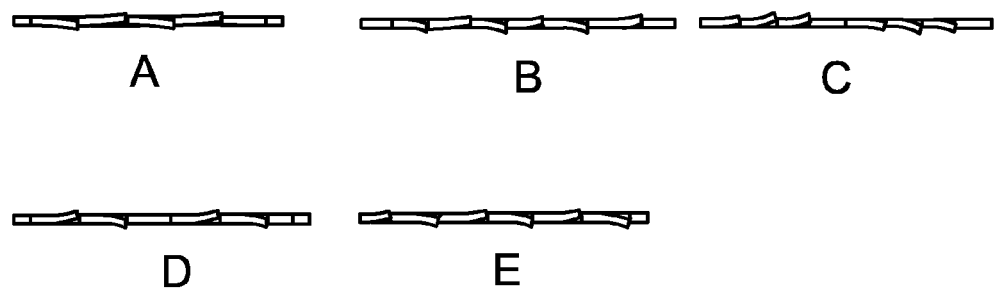
FIGS. 2A-2E show blade configurations, according to some embodiments.
Figure 3:
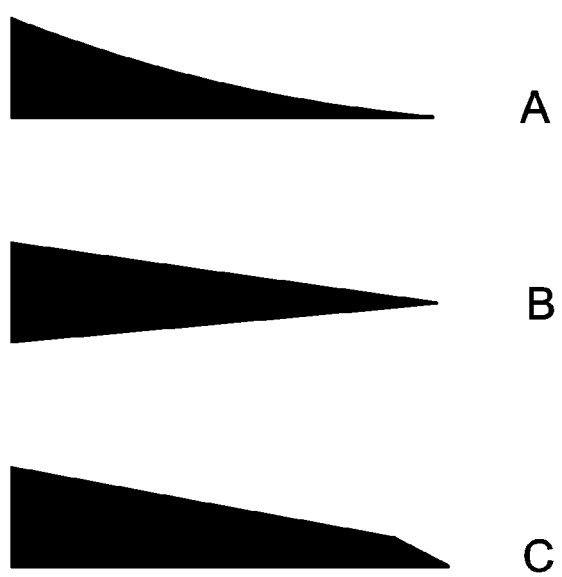
FIGS. 3A-3C show cross section of individual blade profiles, according to some embodiments.

FIGS. 2A-2E show blade configurations, according to some embodiments. FIG. 2A shows a 5 tooth shift pattern of toward, away, toward, away, no shift, repeat. FIG. 2B shows a random shift pattern. FIG. 2C shows a wavy shift pattern. FIG. 3D shows a 3 tooth shift pattern of away, toward, no shift, repeat. And, FIG. 3E shows a simple away, toward, repeat shift pattern.

The choice of blade configuration can be combined with a choice of blade profile, in some embodiments. Those of skill in the art of designing cutting blades will appreciate that the cutting heads taught herein can have a variety cutting actions, such as a chisel action, sawing action, slicing action, and ripping action, for example. As such, the blade profile chosen can be varied to use any blade profile known to one of skill. In some embodiments, the teeth are beveled. In some embodiments, the cutting heads have teeth that point backward as well as forward to include forward cutting surfaces in addition to backward cutting "spurs."

As such, the teachings include a tubular cutting head for removing a target tissue of a subject. And, the tube can be an elongated, tubular structure of any shape, such as circular tube, a square tube, a rectangular tube, an elliptical tube, a pentagonal tube, a hexagonal tube, heptagonal, an octagonal tube, and the like, such that any number of sides, curvatures, or combinations thereof can be used in some embodiments. In some embodiments, a circular tube is used.

The cutting heads can have a combination of blade types, for example, forward-cutting blades, backward-cutting blades, and transverse cutting blades, as well as protrusions, hooks, and the like, for grabbing, ripping, or otherwise removing tissue. In some embodiments, the cutting head can have a backward cutting blade for cutting the target tissue in a backward stroke of the cutting head, a transverse cutting blade for cutting the target tissue in a transverse stroke of the cutting head, or a combination thereof. In some embodiments, a transverse cutting blade can be positioned on the blade guard for cutting the target tissue in a transverse stroke of the cutting head.

FIGS. 3A-3C show cross section of individual blade profiles, according to some embodiments. FIG. 3A shows a planar-concave blade profile. FIG. 3B shows a wedge blade profile. And, FIG. 3C shows a chisel blade profile. Likewise, it should be appreciated that the blades can be designed to have any configuration, including a single-edge, double-edge, single barb, double-barb, straight tip, barbed tip, and the like, to assist with any form of tissue removal, including cutting, slicing, chiseling, scraping, gouging, sawing, grinding, and ripping of a tissue for efficiency in removal during a surgery, for example.

Figure 4:
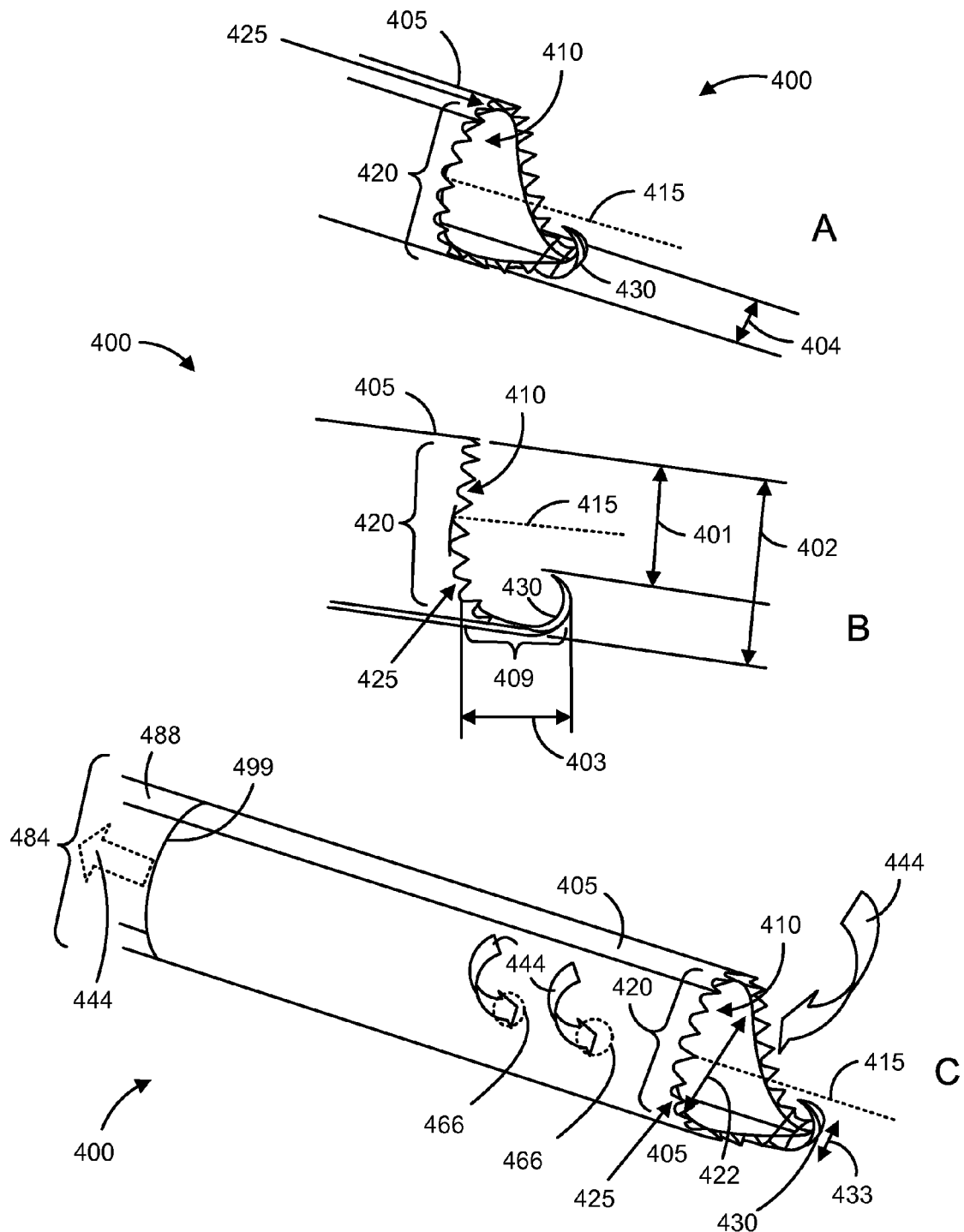
FIGS. 4A-4C illustrate a cutting head, according to some embodiments.

FIGS. 4A-4C illustrate a cutting head, according to some embodiments. FIG. 4A shows an oblique view of the cutting head, and FIG. 4B shows a lateral view. The cutting head 400 can have an outer perimeter 405 that circumscribes a lumen 410 through the cutting head 400, the lumen 410 having a central axis 415. The cutting head 400 can also have a forward cutting blade 420 on a distal edge 425 of the outer perimeter 405, the forward cutting blade 420 configured for (i) cutting a target tissue (not shown) in a forward stroke of the cutting head 400 and (ii) directing the cut tissue into the lumen 410. And, the cutting head 400 can also have a blade guard 430 positioned distal to the forward cutting blade 420 and configured to guard a perimeter tissue (not shown) from the forward cutting blade 420 upon the forward stroke the blade guard 430 having a width 433 that is smaller than the width 422 of a transverse cross-section of the lumen 410 to facilitate entry of the target tissue into the lumen 410 on the forward stroke. And, as shown in FIGS. 4A-4C, the lateral surfaces 409 of the blade guard can also be serrated, or otherwise sharp cutting surfaces, for transverse cutting.

Since the cutting head can be designed to remove tissue through use of a suction 444, the teachings are also directed to systems of a cutting head that operably connect the cutting head with a suction assembly 484 (distal end only shown). As such, FIG. 4C also shows such a surgical, tissue removal system that includes a tubular cutting head 400 for removing a target tissue (not shown) of a subject. The system can include a cutting head 400 having an outer perimeter that circumscribes a flow of suction 444 through the cutting head 400; a lumen 415 circumscribed by the outer perimeter 405, the lumen 410 guiding the flow of suction 444 and having a central axis 415; a forward cutting blade 420 on a distal edge 425 of the outer perimeter 405, the forward cutting blade 420 configured for (i) cutting the target tissue in a forward stroke of the cutting head 400 and (ii) directing the cut tissue into the lumen 410; and, a blade guard 430 positioned distal to the forward cutting blade 420 and configured to guard a perimeter tissue (not shown) from the forward cutting blade 420 upon the forward stroke the blade guard 430.

The cutting head can be configured for an operable communication between the lumen 410 and a source of the suction 444, such that the systems 400 include the suction assembly 484 in operable communication with the cutting head 400 for creating the flow of suction 444 for removing the target tissue through the lumen 410 and out of the subject, the suction assembly 484 comprising a rigid suction tube 488 with a central axis. In some embodiments, the operable communication includes the use of one or more suction ports 466 positioned just proximal to the most proximal point of the distal edge of the out perimeter of the cutting head. In some embodiments, the one or more suction ports 466 can be located from about 3 mm to about 20 mm proximal to the most proximal point of the distal edge 425. While not intended to be bound by any theory or mechanism of action, one of skill will appreciate that a source of additional air can be useful when suctioning within a region that can create vacuum which would otherwise impede or cease the flow of suction that transports excised tissue away from the surgical space during the removal of the tissue. The suction ports 466 can be used to provide the additional air to avoid creating of the vacuum in the surgical space.

Any suction assembly construction known to one of skill can be used in many embodiments. In some embodiments, the suction assembly 484 comprises an at least substantially rigid suction tube 488 having a proximal end (not shown) and a distal end 499, the distal end 499 in the operable communication with the cutting head 400, and the distal end 499 configured for communicating with a source of suction 444 for the suction assembly 484. In some embodiments, the at least substantially rigid suction tube 488 can be formed as a single unit with the cutting head 400. The phrase, "at least substantially rigid" can refer a component that is rigid, or sufficiently rigid such that the desired function is obtained, under the forces that are created with normal use. For example, a desired function may be to prevent or inhibit the occurrence of a bending moment of the rigid component at one or more points along the length of a rigid suction tube upon use of the cutting head in the subject.

The following table describes the dimensional ratios of the cutting head 400 that were found to facilitate fast-and-efficient tissue removal in a discectomy. The "Label" is used to show the components and measures that form the ratios in a small device and a large device.

| | Label | | | | | | |
|---|---|---|---|---|---|---|---|
| | 402 Cutter Diameter (in) | 403 Pincer Height (in) | 404 Pincer Width at the peak of the arch (in) | 401 ID-Pincer Tip gap (in) | 403/ 402 | 404/ 402 | 401/ 402 |
| Small Device | 0.203 | 0.098 | 0.080 | 0.085 | 0.483 | 0.394 | 0.419 |
| Large Device | 0.250 | 0.140 | 0.125 | 0.104 | 0.560 | 0.500 | 0.416 |
| | | | | Mean--> | 0.521 | 0.447 | 0.417 |
| | | | | Theoretical Upper Limit | 0.7 | 0.7 | 0.6 |
| | | | | Theoretical Lower Limit | 0.3 | 0.3 | 0.3 |

The rigid suction tube can comprise any material known to one of skill to be suitable for the uses taught herein. For example, the rigid suction tube can comprise any surgical steel, plastic or resin considered desirable to one of skill for the devices taught herein. In some embodiments, the rigid suction tube can comprise the same or similar materials as the cutting head. In some embodiments, the rigid suction tube can comprise a stainless steel, polyetheretherketone (PEEK), polyimide, or carbon fiber. The wall thickness of the shaft can be any thickness at which a select material will have the physical properties desired. In some embodiments, the wall thickness can range, for example, from 0.003" to 0.020," and from 0.005" to 0.010" in some embodiments. The luminal surface of the tube can be coated with TEFLON, a hydrophobic coating such as parylene, or a hydrophilic coating such as polyvinyl alcohol or polyethylene glycol.

In some embodiments, the rigid suction tube can comprise a polymer tube reinforced with a metal braid, a coiled tube, or a tube with transverse slots to facilitate articulation, should articulation be desired in some embodiments. In such embodiments, the cutting head can be angled relative to the axis of the rigid suction tube by, for example, pulling on a tendon attached to the cutting head on one side, the tendon running-along a guide on the side of the rigid suction tube.

Figure 5:
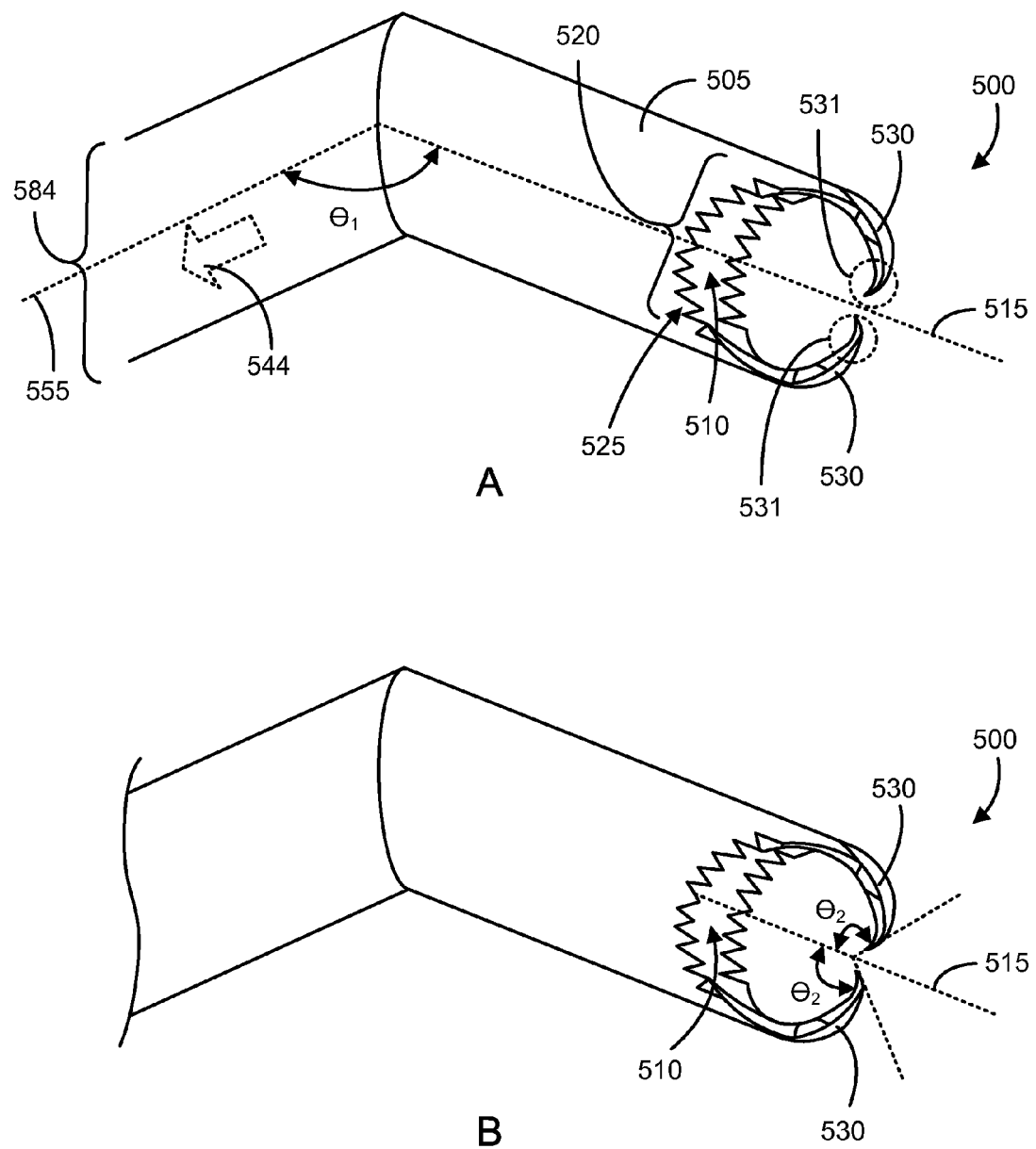
FIGS. 5A and 5B illustrate the angulation of a cutting head 500, according to some embodiments.

FIGS. 5A and 5B illustrate the angulation of a cutting head 500, according to some embodiments. FIG. 5A shows that the central axis 515 of the lumen 510 can be at an angle, $\theta_1$, ranging from about 5° to about 90° from a central axis 555 of the flow of suction 544 at the distal end 599 of the suction assembly (partially shown) 584, and the forward cutting blade 520 can be located about 2 mm to about 25 mm from the vertex of the angle, $\theta_1$. In some embodiments, $\theta_1$ can range from about 2 mm to about 30 mm, from about 2 mm to about 30 mm, from about 2.5 mm to about 25 mm, from about 3 mm to about 25 mm, from about 4 mm to about 20 mm, from about 5 mm to about 15 mm, from about 3 mm to about 25 mm, from about 7 mm to about 12 mm, from about 8 mm to about 10 mm, or any range therein in increments of 0.5 mm.

In some embodiments, the central axis of the lumen is at an angle, $\theta_1$, ranging from about 5° to about 90° from the central axis of the rigid suction tube, and the forward cutting blade is located about 3 mm to about 25 mm from the vertex of the angle, $\theta_1$. And, in some embodiments, the central axis of the lumen has a point of exit at the forward cutting blade, and the point of exit is located at a transverse distance of about 3 mm to about 25 mm that is orthogonal to the central axis of the rigid suction tube In some embodiments, the central axis of the lumen is at an angle, $\theta_1$, ranging from 1° to 180° from a central axis of the flow of suction at the distal end of the suction assembly, and the forward cutting blade is located 3 mm to 25 mm from the vertex of the angle, $\theta_1$. In these embodiments, additional angle, $\theta_3$, is located 5 mm to 25 mm proximal to $\theta_1$, and angles $\theta_1$ and $\theta_3$ are independently selected to range from about 0° to about 180°, with the limitation that (i) the net angle, $\theta_4$, between the central axis of the lumen of the cutting head and the central axis of a rigid suction tube located proximal to $\theta_3$ ranges from 0° to 90°; and, (ii) the distance between the central axis of the lumen of the cutting head and the central axis of the rigid suction tube ranges from 2 mm to 30 mm. As such, the distance in the flow of suction between angles $\theta_1$ and $\theta_3$ can range from about 5 mm to about 30 mm, from about 5 mm to about 25 mm, from about 5 mm to about 20 mm, from about 6 mm to about 18 mm, from about 7 mm to about 15 mm, or any range or distance therein in increments of 1 mm.

In some embodiments, the operable communication between the cutting head 500 and the suction assembly 584 can be articulating, and the angle, $\theta_1$, can be adjustable. In some embodiments, the operable communication between the cutting head 500 and the suction assembly 584 can be rigid, and the angle, $\theta_1$, can be fixed. In some embodiments, the angle, $\theta_1$, can range from 0° to about 45°, from about 1° to about 40°, from about 5° to about 35°, from 10° to about 35°, from 15° to about 40°, from 20° to about 30°, or any range therein in increments of 1°. In some embodiments, the angle, $\theta_1$, can be about 3°, about 5°, about 10°, about 15°, about 20°, about 25°, about 30°, about 35°, about 40°, about 45°, or any angle therein in increments of 1°.

In some embodiments, the backward cutting blade can be positioned on the distal edge 525 of the outer perimeter 505 for cutting the target tissue in the backward stroke of the cutting head 500. In some embodiments, the backward cutting blade 531 can be positioned on the blade guard 530 for cutting the target tissue in the backward stroke of the cutting head 500. FIG. 5B shows that the blade guard 530 can have a double-edged blade tip as the backward cutting blade 531 point back into the lumen 515 at an angle, $\theta_2$, of greater than 90° from the central axis 515 of the lumen 500 to trap and/or cut tissue in the lumen 510 in the backwards stroke of the cutting head 500. The backward cutting blade 531 can be referred to as a "talon" in some embodiments, or "pincer", as it can function to grab, shear, and hook tissue for removal.

It should be appreciated that the cutting heads and systems taught herein have a variety of applications known to one of skill. In some embodiments, the target tissue can be a nucleus pulposus, and the perimeter tissue can be an annulus fibrosis, for example.

A surgical, tissue removal system for a discectomy is provided, and the systems can comprise a tubular cutting head for removing a nucleus pulposus from a subject. In these embodiments, the systems can include a cutting head having an outer perimeter that circumscribes a flow of suction through the cutting head; a lumen circumscribed by the outer perimeter, the lumen guiding the flow of suction; a forward cutting blade on a distal edge of the outer perimeter, the forward cutting blade configured for (i) cutting the nucleus pulposus in a forward stroke of the cutting head and (ii) directing the cut nucleus pulposus into the lumen; a backward cutting blade for cutting the nucleus pulposus in a backward stroke of the cutting head; a transverse cutting blade for cutting the nucleus pulposus in a transverse stroke of the cutting head; and, a blade guard positioned distal to the forward cutting blade and configured to guard an annulus fibrosis tissue from the forward cutting blade upon the forward stroke.

Another valuable feature is that the devices taught herein can operate without substantial clogging from the flow of excised tissue from the cutting head, and this was accomplished by design. Without intending to be bound by any theory or mechanism of action, it was discovered that the area of a transverse cross-section of the distal end of the cutting head should be at least substantially equal to, or less than, the transverse cross-sectional area of any point that is positioned proximal to the distal end of the cutting head leading to collection of the flow of excised tissue from the cutting head. Such points would include, for example, any such point of cross-section along the rigid suction tube, or any other component of the section assembly leading to the point of collection of the excised tissue, for example, the most proximal orifice at which the pressure difference dumps the excised tissue into a collection canister in some embodiments. The term "at least substantially equal to" means that there may be a smaller transverse cross-sectional area, as long as it is limited in magnitude, in some embodiments. In some embodiments, the transverse cross-sectional area can be at least substantially equal to the transverse cross-sectional area of the cutting head if it is no more than 20% less in transverse cross-sectional area at the proximally located cross-section. In some embodiments, the transverse cross-sectional area can be at least substantially equal to the transverse cross-sectional area of the cutting head if it is no more than about 3%, about 5%, about 7%, about 9%, about 11%, about 13%, about 15%, about 17%, about 19%, about 21%. Any percent therein in increments of 1%, less in transverse cross-sectional area at the proximally located cross-section.

The teachings also include a method of removing a target tissue from a subject. In these embodiments, the method can comprise creating an opening in a subject for access to a target tissue; inserting a cutting head taught herein through the opening to access the target tissue in the subject; imaging the depth of the tip of the cutting head using a suitable imaging technique, such as fluoroscopy; and, forcing the cutting head in a forward direction on a surface comprising the target tissue to remove the target tissue while vacuum is activated to suck cut tissue proximally. The forward direction can include a force vector that moves (i) at least substantially on a plane containing the central axis of the lumen of the cutting head, (ii) at least substantially on the surface comprising the target tissue, and (iii) toward the perimeter tissue that is protected by the blade guard. And, the method can include capturing the target tissue in the lumen of the cutting head, as well as removing the target tissue through the lumen and out of the subject.

The phrase, "at least substantially on . . . ," can refer to a position or movement that is sufficient close to the exact desired position such that the desired function is obtained, under the forces and conditions that are created with normal use of the systems and devices taught herein. For example, "at least substantially on a plane containing the central axis of the lumen of the cutting head" or at least substantially on the surface comprising the target tissue" can refer to a position or movement that is parallel or substantially parallel to the plane or surface but perhaps off by about 1 um to about 15 mm from the actual plane, or perhaps off by about 0.1° to about 20° in direction of movement. The measure of "at least substantially" is used to approximate situations in which the exact measure or position is not obtained, but function desired by a person of ordinary skill is obtained. For example, a reduction of outcome when compared to the best possible outcome can be used to determine what is "at least substantially" the desired outcome. In some embodiments, the desired outcome is at least substantially obtained where the best possible outcome is reduced by less than 10%, less than 15%, less than 20%, less than 30%, less than 40% or less than 50%. In some embodiments, the desired outcome is at least substantially obtained where the best possible outcome is reduced by an amount of about 5% to about 30%, about 7% to about 35%, about 10% to about 25%, or any range therein in increments of 1%.

In a discectomy, the opening in the subject can vary, depending on the disk height of the subject, which is often in the range of about 5 mm-7 mm. In some embodiments, the opening in the subject can range in size from about 4 mm×4 mm to about 14 mm×14 mm. In some embodiments, the opening can be about 10 mm×7 mm.

In some embodiments, the method comprises forcing a cutting head taught herein in a backward direction on a surface comprising the target tissue to remove the target tissue. The backward direction can include a force vector that moves (i) at least substantially on a plane containing the central axis of the lumen of the cutting head, (ii) at least substantially on the surface comprising the target tissue, and (iii) away from the perimeter tissue that is protected by the blade guard.

In some embodiments, the method comprises forcing a cutting head taught herein in a transverse direction on a surface comprising the target tissue to remove the target tissue. The transverse direction, for example, can include a force vector that moves (i) at an angle ranging from about 15° to about 165° from a plane containing the central axis of the lumen of the cutting head, (ii) at least substantially on the surface comprising the target tissue, and (iii) in contact with the perimeter tissue that is protected by the blade guard.

The cutting heads taught herein are sharp and can be harmful to tissues during entry and exit of the cutting heads through the surgical opening. An obturator, guard cannula is provided in some embodiments to protect a subject during entry and exit of an elongated surgical cutting device having a non-linearity.

Figure 6:
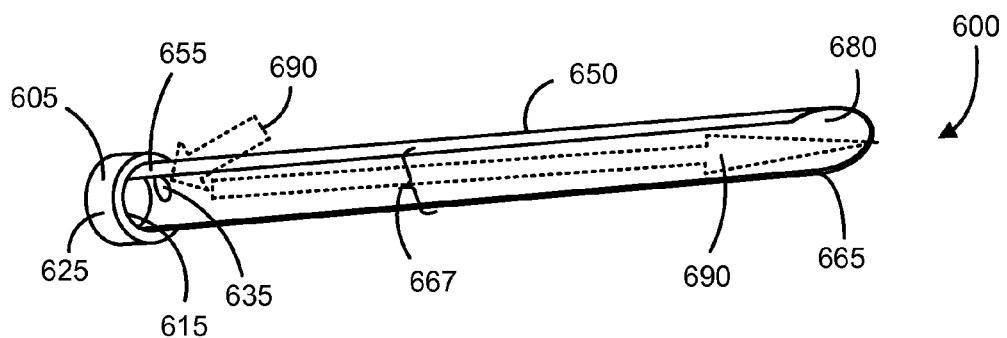
FIG. 6 illustrates an obturator, guard cannula, according to some embodiments.

FIG. 6 illustrates an obturator, guard cannula, according to some embodiments. The guard cannula 600 can comprise an entry hub 605 having an inner perimeter 615, an outer perimeter 625, and an irrigation port 635 that communicates between the inner perimeter 615 with the outer perimeter 625; and, a linear, elongated split-tube 650 having a proximal end 655, a distal end 665, and a lumen 675. In these embodiments, the proximal end 655 of the split-tube 650 can (i) circumscribe at least a portion of the inner perimeter 615 of the hub 605 and (ii) be in operable communication with the irrigation port 635. In these embodiments, the communication can be operable to receive an irrigation fluid 690 from the irrigation port 635, the transport of the irrigation fluid 690 to a target tissue (not shown) including, for example, a movement of the irrigation fluid 690 from the irrigation port 635 to the distal end 665 of the split-tube 650 on a luminal surface 680 of the split-tube 650.

One of skill will appreciate that the "irrigation fluid" can be any fluid desired by one of skill, including liquids and gases. In some embodiments, the irrigation fluid can be aqueous. In some embodiments, the irrigation fluid can be non-aqueous. And, in some embodiments, the irrigation fluid can be an emulsion. In some embodiments, the irrigation fluid can comprise a gas. Examples of aqueous irrigation fluids include water, saline, or an aqueous surfactant containing liquid. Examples of non-aqueous fluids can include any oil-based liquid that may help facilitate tissue extraction during a surgical procedure. Examples of gases can include carbon dioxide, nitrogen, air, and any inert or at least substantially non-reactive gases. In some embodiments, the irrigation fluid can include a lubricant, such as glycerin, silicon oil, and the like. Irrigation fluids can be used as a carrier to help remove an excised tissue, or to help inhibit the creation of a vacuum within a surgical site that can inhibit the removal of the excised tissue. An example of such as a vacuum is one that may be created during use of a suction within a closed cavity such as an intervertebral space within an annulus during a discectomy.

The distal end 665 of the split-tube 650 can also have any configuration desired by one of skill. For example, the distal end 665 can be at least substantially pointed and/or non-blunt. In some embodiments, the distal end 665 can be at least substantially blunt to avoid damage to an entry tissue upon contact of the distal end 665 with the entry tissue. The split-tube 650 can also have a length ranging from about 10 cm to about 60 cm and a width ranging from about 5 mm to about 16 mm. Moreover, the split in the split-tube 650 can compose a gap 667 having a width ranging from about 4 mm to about 14 mm, the split accommodating a non-linearity in the surgical device. In some embodiments, the cutting heads taught herein can have a diameter that is smaller than that of the portion of the suction assembly that passes through the lumen of the guard cannula, such that the guard cannula holds the suction assembly 484 but allows the cutting head 400 to pass through the gap 667. As such, the gap 667 can have a width that exceeds the diameter of the cutting head 400 but is less than the diameter of the rigid suction tube 488, and the lumen of the guard cannula 600 has a diameter that exceeds the diameter of the rigid suction tube 488.

As described above, the systems taught herein can be used in a variety of procedures for removal of a target tissue from a subject including, for example, removal of a meniscus or a discectomy. In some embodiments, the surgical cutting device used with the guard cannula can be a discectomy device. And, in some embodiments, the entry tissue includes the subject's epithelial tissue, muscle tissue, nerve tissue, connective tissue, a blood vessel, bone, cartilage, or a combination thereof, leading to the nucleus pulposus. As such, the target tissue can include the nucleus pulposus in some embodiments.

A surgical tissue removal kit having a surgical tissue removal system and a guard cannula is provided, the kit using any combination of system and cannula embodiments taught herein. In some embodiments, the kits can be a discectomy kit. As such, in some embodiments, the entry tissue includes the subject's epithelial tissue, muscle tissue, nerve tissue, connective tissue, a blood vessel, bone, cartilage, or a combination thereof, leading to the nucleus pulposus. As such, the target tissue can include the nucleus pulposus in some embodiments.

Figure 7:
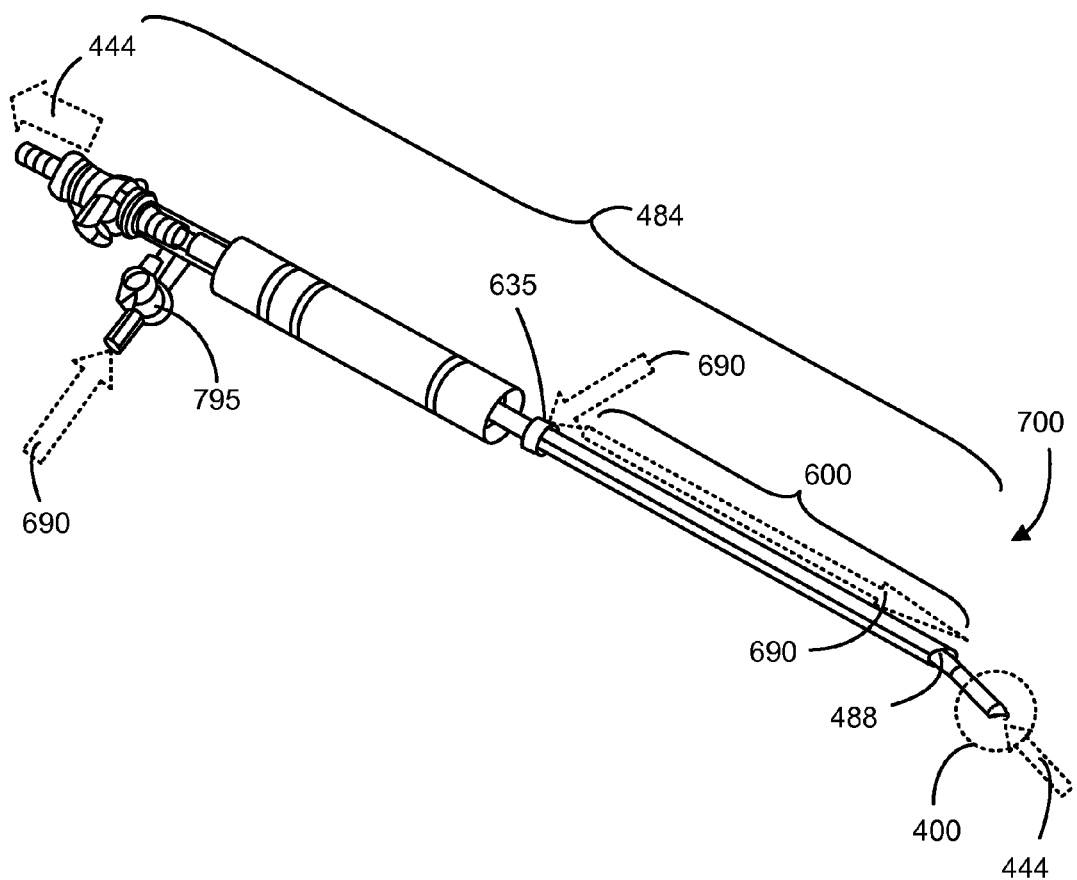
FIG. 7 illustrates a surgical tissue removal kit, according to some embodiments.

FIG. 7 illustrates a surgical tissue removal kit, according to some embodiments. The kit 700 includes a cutting head 400, a suction assembly 484, and an obturator, guard cannula 600. A flow of suction 444 from the suction assembly 484 enters the cutting head 400 to remove a target tissue excised by the cutting head. Irrigation water 690 can enter irrigation valve 795 and/or the irrigation port 635, the irrigation water 690 coming from the irrigation valve 795 is used when the suction 444 is off, and the irrigation water 690 coming from the irrigation port 635 can be used when the suction 444 is on, during which the suction 444 draws the irrigation water 690 between the luminal surface of the guard cannula 600 and the suction assembly 484 into the surgical area (not shown). The guard cannula 600 protects the entry tissue (not shown) while the cutting head 400 and suction assembly 484 moves relative to the entry tissue during a surgical procedure, the cutting head 400 moving, for example, in a forward, backward, and/or transverse motion to excise and remove the target tissue.

A method of using the kits to remove a target tissue is provided. In some embodiments, the method comprises creating an opening in a subject for access to a target tissue; inserting the cutting head of the kit through the entry hub and the elongated split-tube of the guard cannula of the kit; inserting the cutting head of the kit through the opening to access the target tissue in the subject while protecting the entry tissue with the blunt, distal end of the split-tube. Otherwise, methods of using the tissue removal systems are the same or similar to those taught herein. One of skill will appreciate having such kits for discectomies, for example, in which the target tissue can be a nucleus pulposus, and the perimeter tissue can be an annulus fibrosis. One of skill will also appreciate having a kit with a guard cannula that helps protect the subject's epithelial tissue, muscle tissue, nerve tissue, connective tissue, a blood vessel, bone, cartilage, or a combination thereof, leading to the nucleus pulposus in such procedures.

Figure 8:
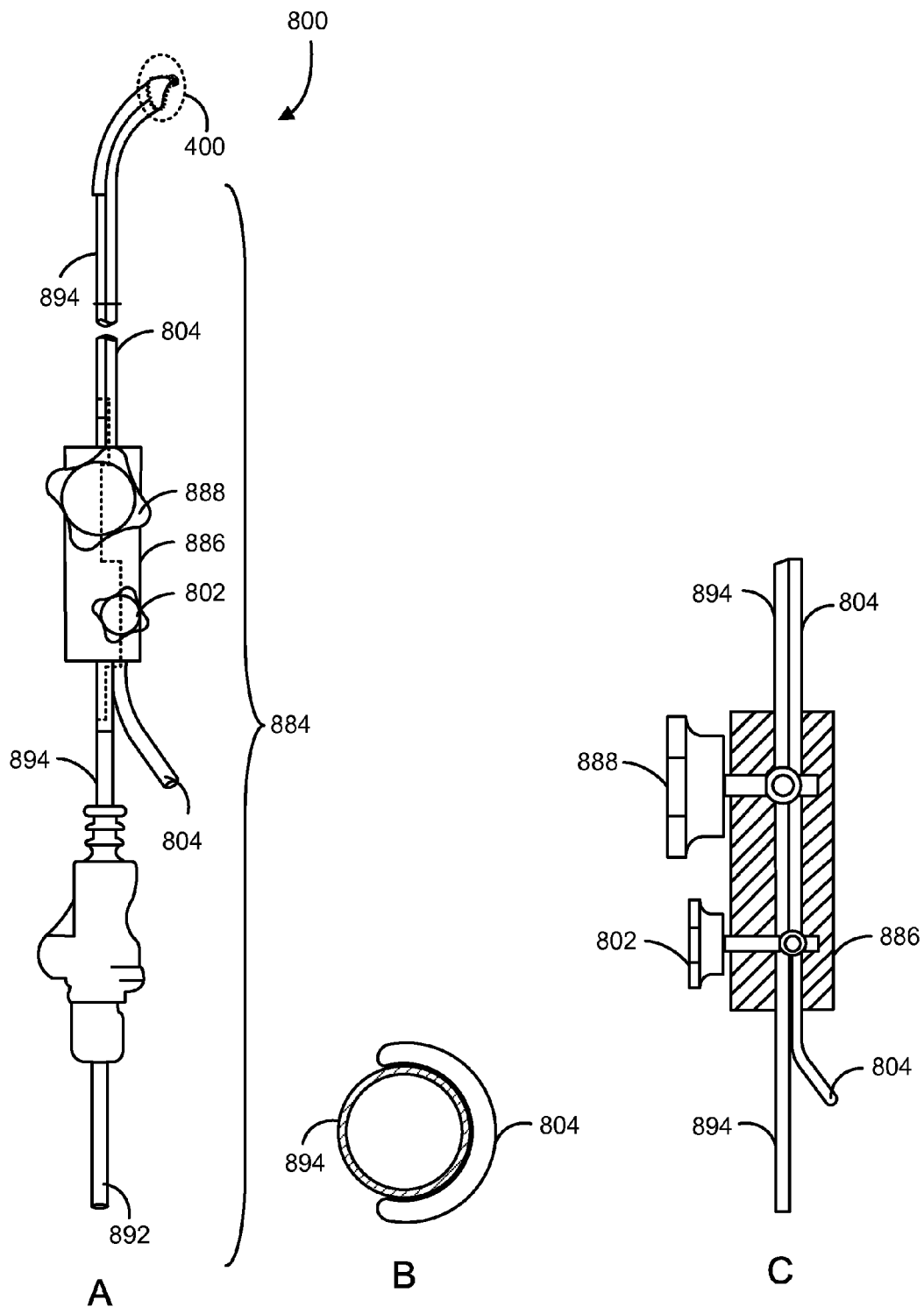
FIGS. 8A-8C illustrate a system or kit that can irrigate concurrent with application of suction, and without the obturator, guard cannula in place, according to some embodiments.

FIGS. 8A-8C illustrate a system or kit that can irrigate concurrent with application of suction, and without the obturator, guard cannula in place, according to some embodiments. FIG. 8A shows the complete discectomy system 800 including the cutting head 400, a means for applying suction through the suction assembly 884, a control handle 886 and a vacuum attachment 892, an irrigation tube 804, an irrigation control 802, and an optional vacuum control 888.

In embodiments in which the cutting head angle is adjustable, the handle 886 can have a knob (not shown) that turns to tension a pull cable to flex or straighten the cutting head relative to the rigid suction tube, or a slide that tensions the cable to flex or straighten the cutting head relative to the rigid suction tube. The cables to flex and straighten can be on opposing sides of the shaft constrained to small side lumens attached to the outer surface of the shaft to flex and straighten out the cutting head.

FIG. 8B shows a cross-sectional view of the irrigation tube 804 relative to the rigid suction tube 894. And, FIG. 8C shows a cross-sectional view of the control handle 886 and internal piping.

One of skill will appreciate that the teachings and examples provided herein are directed to basic concepts that can extend beyond any particular embodiment, embodiments, figure, or figures. It should be appreciated that any examples are for purposes of illustration and are not to be construed as otherwise limiting to the teachings.

EXAMPLE 1

Testing of Cutter Head Designs

A variety of cutter heads were tested in 3 cadaver laboratories on 28 discs. The results were compared to determine the most efficient cutter head design. A desirable cutter head design was one that would cut well on all target tissues, including the nucleus pulposus, vertebral endplates, and inner annulus tissue. However, the cutter head should also cut the target tissues in a desired manner while providing little to no damage to the perimeter tissue, such tissue including the perimeter annulus fibrosis tissue that should be preserved as a desirable perimeter structure. In addition, the design should remove tissue quickly under suction, such that the configuration of the head facilitates the removal of the tissue under suction.

Figure 9:
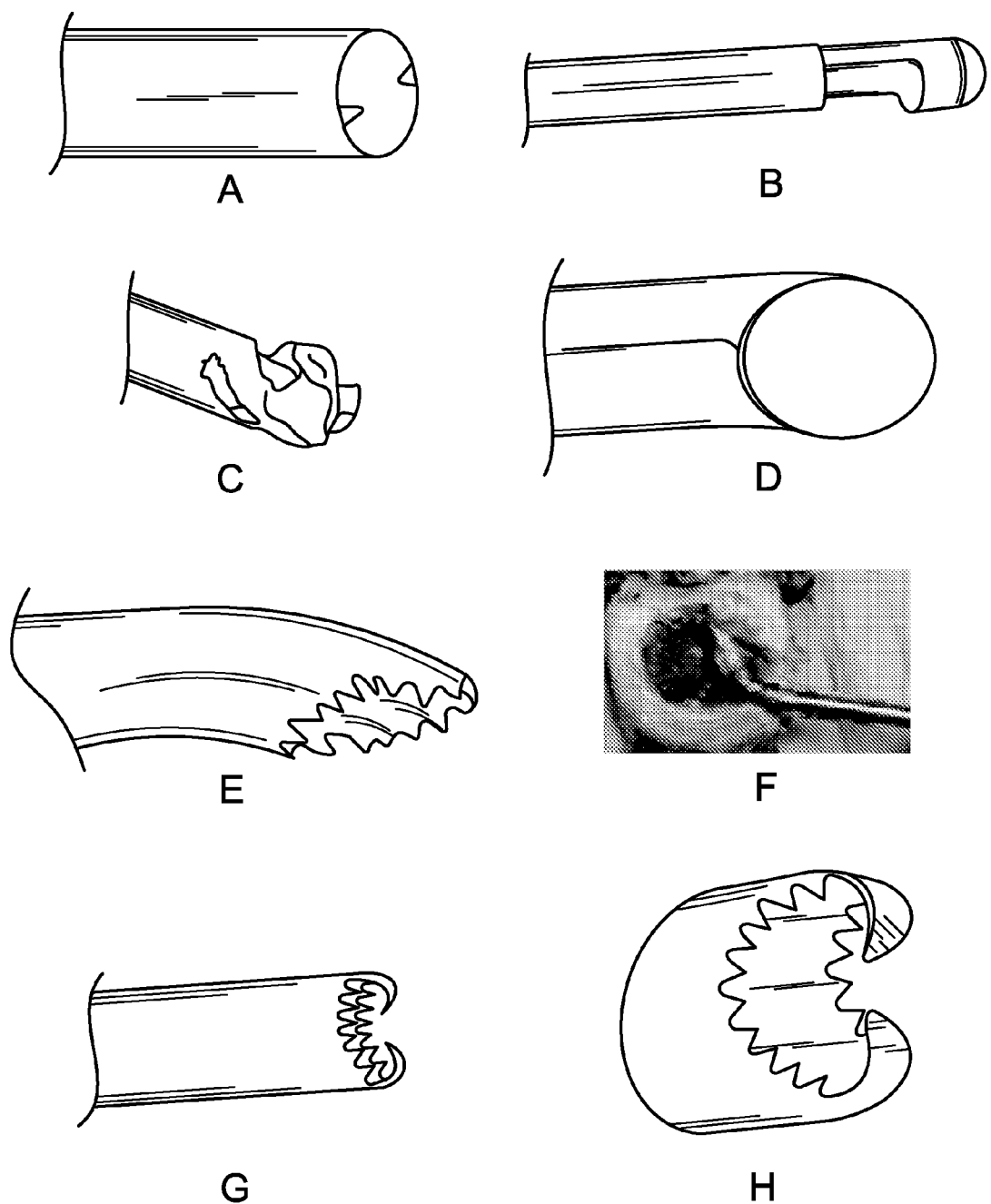
FIGS. 9A-9H show cutting head designs that were tested, according to some embodiments.

FIGS. 9A-9H show cutting head designs that were tested, according to some embodiments. The design in FIG. 9A cut well but it was not as safe to the annulus as other designs. The design in FIG. 9B was safe to the annulus but it did not cut tough tissue well and showed too much resistance. The design in FIG. 9C also did not penetrate tough tissue well. The design in FIG. 9D did cut and decorticate well, but it clogged on soft/elastic tissue. The design in FIG. 9E cut tough tissue well and did not clog, and it also decorticates really well. It was also safe to the annulus. The shape of the device however, did not reach the far side of the nucleus pulposus. The design in FIG. 9F shows a bend that was introduced to the device to enable the cutting head of FIG. 9E to reach the far side of the nucleus pulposus. The design in FIGS. 9G and 9H, however, showed the most efficient cutting head performance identified in the testing, removing 23 cc of material in 5 minutes.

EXAMPLE 2

This example further developed the designs of the cutting heads. The design in FIGS. 8G and 8H were further investigated in 7 cadaver labs and 28 discs.

Figure 10:
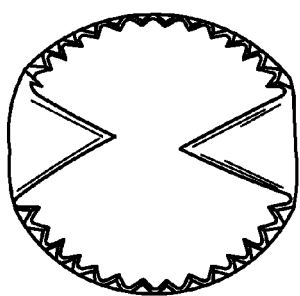
FIGS. 10A-10E illustrate the advancements in the cutting head, according to some embodiments.
Figure 10:
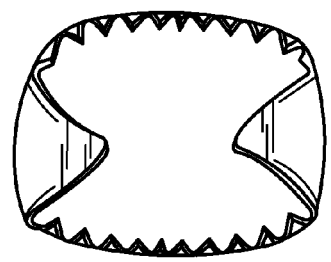
Figure 10:
Figure 10:
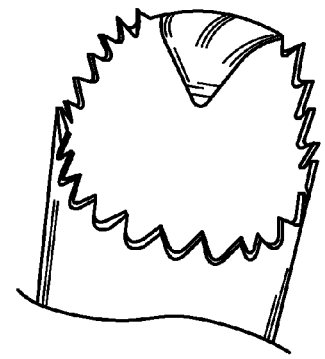
Figure 10:
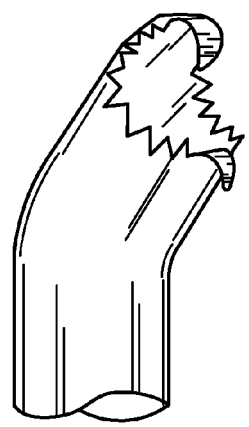

FIGS. 10A-10E illustrate the advancements in the cutting head, according to some embodiments. The design in FIG. 10A shows a cutting head having a bevel on the outer surface of the cutting teeth, and the device cut poorly and gouged soft bone. The design in FIG. 10B shows an oval cutting head not having the bevel on the outer surface of the cutting teeth, and the device had inconsistent cutting and gouged soft bone. The design in FIG. 10C was shown for a comparison result using a ring curette, and the device gouged soft bone. The design in FIG. 10D shows a short cutting head with a single "talon" or pincer, and the device showed the most appealing results to date with optimal cutting and no gouging. FIG. 10E is another proposed design, configured to perform with the efficiency of the design of FIG. 10D, with the addition of a second talon that bends away from the lumen of the cutting head to serve as an additional talon and blade guard.

The method used in this example was as follows:
1. Cutting a pilot hole of a 5-8 mm dimension in height and width;
2. Pointing a 15° tip parallel to the vertebral endplates to cut and expand the cavity medially and laterally;
3. Gradually shaving down the endplates to hard tissue (cartilage or bone); fluoroscopy was used to verify the depth of the tip; the tip was used to shave along the curvature of the endplate; shaving was stopped where bone was exposed (hard, rough, sticky, and red aspirate identified as the endpoint); and, the handle of the device is tilted (i) medially to decorticate lateral side, and (ii) laterally to decorticate medial side;
4. Sweeping the cutting head medially-lateraly against anterior annulus to remove nucleus attached to the annulus and inner annulus as needed;
5. Pointing a 40° tip contralaterally and start shaving from posterior annulus while tilting handle laterally to remove bulk nucleus; and,
6. Rotating the handle toward the endplate to further decorticate.

EXAMPLE 3

This example describes an alternate embodiment that was tested, referred to as the serpentine or bayonet configuration, in which the rigid suction tube 488 can have at least two angles; an angle $\theta_1$, and an angle $\theta_3$.

Figure 11:
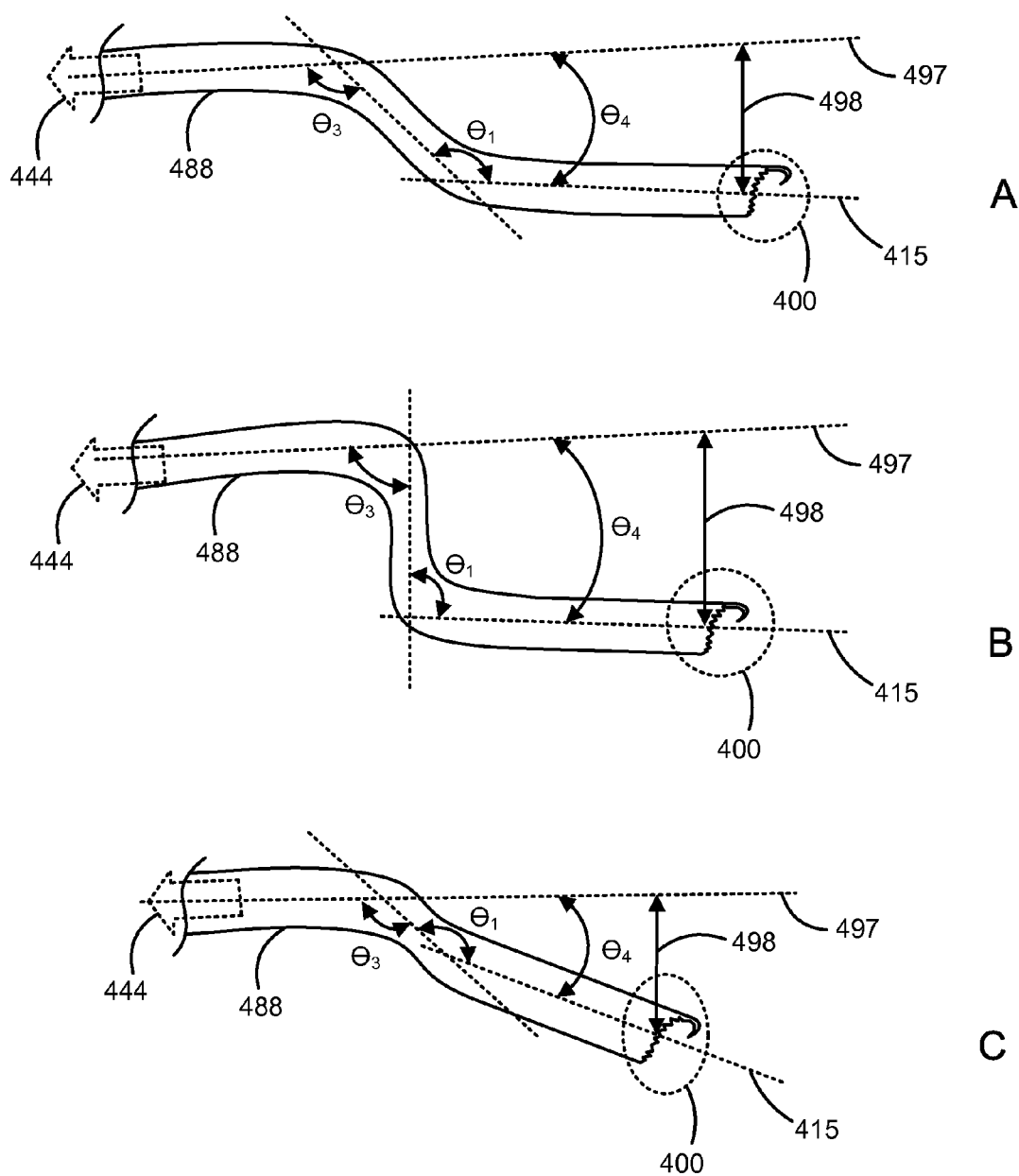
FIGS. 11A-11C illustrate a bayonet-type communication between a cutting head and a suction assembly, according to some embodiments.

FIGS. 11A-11C illustrate a bayonet-type communication between a cutting head and a suction assembly, according to some embodiments. It was discovered that the distal end of the rigid suction tube 488 can be redirected in bayonet, or serpentine, fashion in order to facilitate an improved access of the cutting head to a target tissue during a discectomy, for example. As shown in FIGS. 11A-11C, Angles $\theta_1$ and $\theta_3$ can each be independently selected to range from about 0° to about 180°, with the limitation that (i) the net angle, $\theta_4$, that is realized between the central axis 415 of the lumen 410 of the cutting head 400 and the central axis 497 of the rigid suction tube 488 (extended as directed proximal to $\theta_1$) ranges from 0° to 90°; and, (ii) the distance 498 between the central axis 415 of the lumen 410 of the cutting head 400 and the central axis 497 of the rigid suction tube 488 can range from about 2 mm to about 30 mm. And, in these embodiments, the central axis of the lumen can have a point of exit at the forward cutting blade, and the point of exit is located at a transverse distance of about 3 mm to about 25 mm In some embodiments, the distance 498 between the from about 2.5 mm to about 25 mm, from about 3 mm to about 25 mm, from about 4 mm to about 20 mm, from about 5 mm to about 15 mm, from about 3 mm to about 25 mm, from about 7 mm to about 12 mm, from about 8 mm to about 10 mm, or any range therein in increments of 0.5 mm. As such, the distance 498 can be about 2 mm, about 3 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 22 mm, about 24 mm, about 26 mm, about 28 mm, about 30 mm, and any distance or range therein in increments of 0.5 mm. In some embodiments, the distance between the vertex of $\theta_3$ and the distal end of the cutting head 400 can range from about 5 mm to about 25 mm, from about 6 mm to about 20 mm, from about 7 mm to about 15 mm, or any range therein in increments of 1 mm.

I claim:
1. A tubular cutting head for removing a nucleus pulposus of a subject, the cutting head comprising
   an outer perimeter that circumscribes a lumen through the cutting head, the lumen having a central axis and in an operable communication with an at least substantially rigid tube; and,
   a cutting surface on a distal perimeter of the cutting head, the cutting surface having
      a forward cutting blade having a forward-directed cutting surface on a distal edge of the outer perimeter, the forward cutting blade configured for (i) cutting the nucleus pulposus tissue in a forward stroke of the cutting head and (ii) excising and directing entry of the excised nucleus pulposus tissue into the lumen on the forward stroke;
      and,
      a blade guard positioned distal to the forward cutting blade and configured to guard an annulus fibrosis tissue from the forward cutting blade upon the forward stroke, the blade guard configured with
         a first laterally-directed cutting surface configured for cutting the nucleus pulposus in a first transverse stroke of the cutting head in a first transverse direction, the first laterally-directed cutting surface adapted as a directional shift from the forward cutting direction of the forward cutting blade to the first transverse direction of the first laterally-directed cutting surface, the first laterally-directed cutting surface including an apex pointing away from a plane that geometrically bisects the blade guard and the central axis; and,
         a second laterally-directed cutting surface opposing the first laterally-directed cutting surface and configured for cutting the nucleus pulposus in a second transverse stroke of the cutting head in a second transverse direction, the second laterally-directed cutting surface adapted as a directional shift from the forward cutting direction of the forward cutting blade to the second transverse direction of the second laterally-directed cutting surface, the second laterally-directed cutting surface including an apex pointing away from the plane that geometrically bisects the blade guard and the central axis.

2. The cutting head of claim 1, wherein the blade guard also has a backward cutting blade having a backward-directed cutting surface and configured with a barb to hook nucleus pulposus tissue for removal of the nucleus pulposus tissue in a backward stroke of the cutting head.

3. The cutting head of claim 1, wherein the first laterally-directed cutting surface, second laterally-directed cutting surface, or both also has a plurality of laterally-directed, serrated cutting surfaces.

4. The cutting head of claim 1, wherein the blade guard also has a backward cutting blade having a backward-directed cutting surface and configured with a barb to hook nucleus pulposus tissue for removal of the nucleus pulposus tissue in a backward stroke of the cutting head; and, a plurality of sharp lateral cutting surfaces positioned on the blade guard, each of the lateral cutting surfaces adapted as the directional shift from a forward-directed cutting surface of the forward cutting blade.

5. The cutting head of claim 1, wherein the cutting head is formed from a single tube.

6. A surgical, nucleus pulposus removal system, comprising:
- a tubular cutting head adapted for removing a target tissue of a subject, the cutting head having
  - an outer perimeter that circumscribes a lumen through the cutting head, the lumen having a central axis and in an operable communication with an at least substantially rigid tube;
  - a cutting surface on a distal perimeter of the tubular cutting head, the cutting surface having
    - a forward cutting blade having a forward-directed cutting surface on a distal edge of the outer perimeter, the forward cutting blade configured for (i) cutting the nucleus pulposus tissue in a forward stroke of the cutting head and (ii) excising and directing entry of the excised nucleus pulposus tissue into the lumen on the forward stroke; and,
    - a blade guard positioned distal to the forward cutting blade and configured to guard an annulus fibrosis tissue from the forward cutting blade upon the forward stroke, the blade guard configured with
      - a first laterally-directed cutting surface configured for cutting the nucleus pulposus in a first transverse stroke of the cutting head in a first transverse direction, the first laterally-directed cutting surface adapted as a directional shift from the forward cutting direction of the forward cutting blade to the first transverse direction of the first laterally-directed cutting surface, the first laterally-directed cutting surface including an apex pointing away from a plane that geometrically bisects the blade guard and the central axis; and,
      - a second laterally-directed cutting surface opposing the first laterally-directed cutting surface and configured for cutting the nucleus pulposus in a second transverse stroke of the cutting head in a second transverse direction, the second laterally-directed cutting surface adapted as a directional shift from the forward cutting direction of the forward cutting blade to the second transverse direction of the second laterally-directed cutting surface, the second laterally-directed cutting surface including an apex pointing away from the plane that geometrically bisects the blade guard and the central axis,
  - wherein, the cutting head is configured for an operable communication between the lumen and a source of a suction, the outer perimeter adapted to circumscribe a flow of suction through the cutting head; and,
- a suction assembly in operable communication with the cutting head, the suction assembly comprising an at least substantially rigid suction tube with a central axis and creating the flow of suction for removing the excised nucleus pulposus tissue through the lumen and out of the subject.

7. The system of claim 6, wherein the blade guard is also the backward cutting blade, the guard having a double-edged blade tip that points back into the lumen at an angle, $\theta_2$, of greater than 90° to trap tissue, cut tissue, or trap and cut tissue in the lumen in the backwards stroke of the cutting head.

8. The system of claim 6, wherein the central axis of the lumen is at an angle, $\theta_1$, ranging from about 5° to about 90° from the central axis of the rigid suction tube, and the forward cutting blade is located about 3 mm to about 25 mm from the vertex of the angle, $\theta_1$.

9. The system of claim 6, wherein the central axis of the lumen has a point of exit at the forward cutting blade, and the point of exit is located at a transverse distance of about 3 mm to about 25 mm that is orthogonal to the central axis of the rigid suction tube.

10. The system of claim 6, wherein the central axis of the lumen is at an angle, $\theta_1$, ranging from 1° to 180° from the central axis of the rigid suction tube, and the forward cutting blade is located 3 mm to 25 mm from the vertex of the angle, $\theta_1$; wherein, an additional angle, $\theta_3$, is located 5 mm to 25 mm proximal to $\theta_1$;
- angles $\theta_1$ and $\theta_3$ are independently selected to range from about 0° to about 180°, with the limitation that
  - (i) the net angle, $\theta_4$, between the central axis of the lumen of the cutting head and the central axis of the rigid suction tube located proximal to $\theta_3$ ranges from 0° to 90°; and,
  - (ii) the central axis of the lumen has a point of exit at the forward cutting blade, and the point of exit is located at a transverse distance of about 3 mm to about 25 mm that is orthogonal to the central axis of the rigid suction tube.

11. The system of claim 6, wherein the cutting head is formed from a single tube.

12. A surgical, tissue removal system for a discectomy, comprising:
- a tubular cutting head adapted for removing a nucleus pulposus tissue from a subject, the cutting head having
  - an outer perimeter that circumscribes a lumen through the cutting head, the lumen having a central axis and in an operable communication with an at least substantially rigid tube;
  - a cutting surface on a distal perimeter of the tubular cutting head, the cutting surface having
    - a forward cutting blade having a forward-directed cutting surface on a distal edge of the outer perimeter and configured for (i) cutting and excising the nucleus pulposus tissue in a forward stroke of the cutting head and (ii) directing entry of the cut and excised nucleus pulposus into the lumen on the forward stroke;
    and,
    - a blade guard positioned distal to the forward cutting blade and configured to guard an annulus fibrosis tissue from the forward cutting blade upon the forward stroke, the blade guard including a transverse cutting blade having a plurality of laterally-directed cutting surfaces including a first laterally-directed cutting surface and a second laterally-directed cutting surface that opposes the first laterally-directed cutting surface, the first laterally-directed cutting surface and the second laterally-directed cutting surface each configured for cutting and excising the nucleus pulposus in a respective first and second transverse stroke of the cutting head, each of the laterally-directed cutting surfaces adapted as a directional shift from the forward-directed cutting surface of the forward cutting blade to a laterally-directed cutting surface, the first laterally-directed cutting surface and the second laterally-directed cutting surface each including an apex pointed away from a plane that geometrically bisects the blade guard and the central axis;
  and,
- a suction assembly in operable communication with the cutting head, the suction assembly comprising an at least substantially rigid suction tube with a central axis and creating the flow of suction for removing the nucleus pulposus tissue through the lumen and out of the subject.

13. The system of claim 12, wherein the central axis of the lumen of the cutting head is at an angle, $\theta_1$, ranging from about 5° to about 90° from the central axis of the rigid suction tube, and the forward cutting blade is located about 3 mm to about 25 mm from the vertex of the angle, $\theta_1$.

14. The system of claim 12, wherein the central axis of the lumen of the cutting head has a point of exit at the forward cutting blade, and the point of exit is located at a transverse distance of about 3 mm to about 25 mm that is orthogonal to the central axis of the rigid suction tube.

15. The system of claim 12, wherein the plurality of cutting surfaces include serrations.

16. The system of claim 12, wherein the central axis of the lumen is at an angle, $\theta_1$, ranging from 1° to 180° from the central axis of the rigid suction tube, and the forward cutting blade is located 3 mm to 25 mm from the vertex of the angle, $\theta_1$; wherein, an additional angle, $\theta_3$, is located 5 mm to 25 mm proximal to $\theta_1$;
angles $\theta_1$ and $\theta_3$ are independently selected to range from about 0° to about 180°, with the limitation that
(i) the net angle, $\theta_4$, between the central axis of the lumen of the cutting head and the central axis of the rigid suction tube located proximal to $\theta_3$ ranges from 0° to 90°; and,
(ii) the central axis of the lumen has a point of exit at the forward cutting blade, and the point of exit is located at a transverse distance of about 3 mm to about 25 mm that is orthogonal to the central axis of the rigid suction tube.

17. The system of claim 12, further comprising a backward cutting blade having a backward-directed cutting surface and configured with a barb to hook nucleus pulposus tissue for removal of the nucleus pulposus tissue in a backward stroke of the cutting head, wherein the backward cutting blade is configured as a talon, positioned on the distal edge of the outer perimeter for cutting the nucleus pulposus tissue in the backward stroke of the cutting head.

18. The system of claim 12, wherein the blade guard is also a backward cutting blade, the guard having a double-edged blade tip point back into the lumen at an angle, $\theta_2$, of greater than 90° to trap tissue, cut tissue, or trap and cut tissue in the lumen in the backwards stroke of the cutting head.

19. The system of claim 12, wherein the cutting surface is serrated, and the transverse cutting blade has two opposing laterally-directed cutting surfaces adapted as a directional shift from the forward-directed cutting surface of the forward cutting blade to each of the two opposing respective sharp laterally-directed cutting surfaces for cutting the nucleus pulposus tissue in the transverse stroke of the cutting head.

20. The system of claim 12, wherein the cutting head is formed from a single tube.

21. A method of removing a nucleus pulposus tissue from a subject, the method comprising:
creating an opening in a subject for access to a nucleus pulposus tissue;
inserting the cutting head of claim 1 through the opening to access the nucleus pulposus tissue in the subject;
forcing the cutting head in a forward direction on a surface comprising the nucleus pulposus tissue to remove the nucleus pulposus tissue, the forward direction including a force vector that moves (i) at least substantially on a plane containing the central axis of the lumen of the cutting head to excise the nucleus pulposus tissue and direct entry of the excised nucleus pulposus tissue into the lumen of the cutting head when forcing the cutting head in the forward direction, (ii) at least substantially on the surface comprising the nucleus pulposus tissue, and (iii) toward the annulus fibrosis tissue that is protected by the blade guard;
capturing the nucleus pulposus tissue in the lumen of the cutting head when forcing the cutting head in the forward direction; and,
removing the excised nucleus pulposus tissue through the lumen and out of the subject through a suction assembly.

22. The method of claim 21, the cutting head further comprising a backward cutting blade having a backward-directed cutting surface and configured with a barb to hook nucleus pulposus tissue for removal of the nucleus pulposus tissue in a backward stroke of the cutting head, and the method further comprising forcing the cutting head in a backward direction on a surface comprising the nucleus pulposus tissue to remove the nucleus pulposus tissue, the backward direction including a force vector that moves (i) at least substantially on a plane containing the central axis of the lumen of the cutting head, (ii) at least substantially on the surface comprising the nucleus pulposus tissue, and (iii) away from the annulus fibrosis tissue that is protected by the blade guard.

23. The method of claim 21, further comprising forcing the cutting head in a transverse direction on a surface comprising the nucleus pulposus tissue to remove the nucleus pulposus tissue, the transverse direction including a force vector that moves (i) at an angle ranging from about 15° to about 150° from a plane containing the central axis of the lumen of the cutting head, (ii) at least substantially on the surface comprising the nucleus pulposus tissue, and (iii) in contact with the annulus fibrosis tissue that is protected by the blade guard.

24. The method of claim 2, wherein the cutting head is formed from a single tube.

* * * * *